US011881221B2

(12) United States Patent
Khaleghi

(10) Patent No.: US 11,881,221 B2
(45) Date of Patent: *Jan. 23, 2024

(54) HEALTH MONITORING SYSTEM AND APPLIANCE

(71) Applicant: The Notebook, LLC, Santa Monica, CA (US)

(72) Inventor: Karen Elaine Khaleghi, Pacific Palisades, CA (US)

(73) Assignee: The Notebook, LLC, Pacific Palisades, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/810,032

(22) Filed: Jun. 30, 2022

(65) Prior Publication Data
US 2023/0162732 A1 May 25, 2023

Related U.S. Application Data

(63) Continuation of application No. 16/776,052, filed on Jan. 29, 2020, now Pat. No. 11,386,896, which is a
(Continued)

(51) Int. Cl.
G10L 15/22 (2006.01)
G10L 25/90 (2013.01)
(Continued)

(52) U.S. Cl.
CPC .............. G10L 15/22 (2013.01); A61B 5/165 (2013.01); A61B 5/4803 (2013.01); B60K 28/06 (2013.01);
(Continued)

(58) Field of Classification Search
CPC . G10L 15/22; G10L 15/1815; G10L 15/1822; G10L 25/24; G10L 25/66;
(Continued)

(56) References Cited

U.S. PATENT DOCUMENTS 3,594,066 A 7/1971 Cook
3,649,765 A 3/1972 Rabiner
(Continued)

FOREIGN PATENT DOCUMENTS

KR 10-2018-0004312 A 1/2018

OTHER PUBLICATIONS

Healow Home Page, dated Apr. 17, 2016, 3 pages—https://web.archive.org/web/20160417210345/https://healow.com/apps/jsp/webview/signIn.jsp.
(Continued)

Primary Examiner — Fariba Sirjani
(74) Attorney, Agent, or Firm — Knobbe, Martens, Olson & Bear LLP

(57) ABSTRACT

Systems and methods are disclosed. A digitized human vocal expression of a user and digital images are received over a network from a remote device. The digitized human vocal expression is processed to determine characteristics of the human vocal expression, including: pitch, volume, rapidity, a magnitude spectrum identify, and/or pauses in speech. Digital images are received and processed to detect characteristics of the user face, including detecting if any of the following is present: a sagging lip, a crooked smile, uneven eyebrows, and/or facial droop. Using the human vocal expression characteristics and face characteristics, a determination is made as to what action is to be taken. A cepstrum pitch may be determined using an inverse Fourier transform of a logarithm of a spectrum of a human vocal expression signal. The volume may be determined using peak heights in a power spectrum of the human vocal expression.

21 Claims, 8 Drawing Sheets

Related U.S. Application Data continuation of application No. 16/286,986, filed on Feb. 27, 2019, now Pat. No. 10,573,314, which is a continuation of application No. 15/908,428, filed on Feb. 28, 2018, now Pat. No. 10,235,998.

(51) Int. Cl.

| | | |
|---|---|---|
| *G10L 25/24* | (2013.01) | |
| *G10L 25/78* | (2013.01) | |
| *G10L 15/18* | (2013.01) | |
| *G10L 25/66* | (2013.01) | |
| *G10L 25/93* | (2013.01) | |
| *A61B 5/00* | (2006.01) | |
| *B60K 28/06* | (2006.01) | |
| *A61B 5/16* | (2006.01) | |
| *G06V 40/16* | (2022.01) | |

(52) U.S. Cl.
CPC .......... *G06V 40/165* (2022.01); *G06V 40/167* (2022.01); *G06V 40/171* (2022.01); *G06V 40/174* (2022.01); *G10L 15/1815* (2013.01); *G10L 15/1822* (2013.01); *G10L 25/24* (2013.01); *G10L 25/66* (2013.01); *G10L 25/78* (2013.01); *G10L 25/90* (2013.01); *G10L 25/93* (2013.01); *G10L 2015/223* (2013.01); *G10L 2015/227* (2013.01)

(58) Field of Classification Search
CPC ......... G10L 25/78; G10L 25/90; G10L 25/93; G10L 2015/223; G10L 2015/227; G06V 40/165; G06V 40/167; G06V 40/171; G06V 40/174
See application file for complete search history.

(56) References Cited

U.S. PATENT DOCUMENTS

| | | | |
|---|---|---|---|
| 4,682,361 A | 7/1987 | Selbach | |
| 5,293,584 A | 3/1994 | Brown | |
| 5,579,393 A | 11/1996 | Conner | |
| 5,633,910 A | 5/1997 | Cohen | |
| 5,699,404 A | 12/1997 | Satyamurti | |
| 5,823,948 A | 10/1998 | Ross | |
| 5,924,074 A | 7/1999 | Evans | |
| 6,039,688 A | 3/2000 | Douglas | |
| 6,047,254 A | 4/2000 | Ireton | |
| 6,234,964 B1 | 5/2001 | Iliff | |
| 6,290,646 B1 | 9/2001 | Cosentino | |
| 6,292,771 B1 | 9/2001 | Haug | |
| 6,411,933 B1 | 6/2002 | Maes | |
| 6,544,294 B1 | 4/2003 | Greenfield | |
| 6,726,636 B2 | 4/2004 | Der Ghazarian | |
| 6,941,271 B1 | 9/2005 | Soong | |
| 7,174,332 B2 | 2/2007 | Baxter | |
| 7,222,075 B2 | 5/2007 | Petrushin | |
| 7,302,490 B1 | 11/2007 | Gupta | |
| 7,647,555 B1 | 1/2010 | Wilcox | |
| 7,770,117 B1 | 8/2010 | Uy | |
| 7,783,072 B2 | 8/2010 | Work | |
| 7,788,605 B1 | 8/2010 | Shoemaker | |
| 8,255,225 B2 | 8/2012 | Byford | |
| 8,374,992 B2 | 2/2013 | Meyyappan et al. | |
| 8,533,511 B2 | 9/2013 | Ma et al. | |
| 8,606,595 B2 | 12/2013 | Udani | |
| 8,775,213 B2 | 7/2014 | Hughes | |
| 8,826,123 B2 | 9/2014 | Audet | |
| 8,868,436 B2 | 10/2014 | Gotthardt | |
| 9,070,357 B1 | 6/2015 | Kennedy | |
| 9,158,335 B2 | 10/2015 | Zheng | |
| 9,252,962 B1 | 2/2016 | Valeti | |
| 9,256,588 B1 | 2/2016 | Moscovich et al. | |
| 9,256,719 B2 | 2/2016 | Serini | |
| 9,305,155 B1 | 4/2016 | Vo | |
| 9,619,616 B2 | 4/2017 | Raduchel | |
| 9,658,756 B2 | 5/2017 | Freeman | |
| 9,733,801 B2 | 8/2017 | Audet | |
| 9,788,799 B2 | 10/2017 | Wagner | |
| 9,899,038 B2 | 2/2018 | Khaleghi | |
| 9,928,379 B1 | 3/2018 | Hoffer | |
| 9,934,793 B2 | 4/2018 | Bae | |
| 9,959,556 B1 | 5/2018 | Cordell | |
| 10,032,120 B2 | 7/2018 | Collins | |
| 10,121,345 B1 | 11/2018 | Fields et al. | |
| 10,235,998 B1* | 3/2019 | Khaleghi | A61B 5/165 |
| 10,402,926 B2 | 9/2019 | Kelly | |
| 10,484,845 B2 | 11/2019 | Khaleghi | |
| 10,516,938 B2 | 12/2019 | Zass | |
| 10,573,314 B2* | 2/2020 | Khaleghi | G10L 25/66 |
| 10,657,166 B2 | 5/2020 | Gorzela | |
| 10,726,393 B2 | 7/2020 | Kaufman | |
| 11,222,716 B2 | 1/2022 | Vozila | |
| 11,386,896 B2* | 7/2022 | Khaleghi | G10L 25/78 |
| 2001/0034639 A1 | 10/2001 | Jacoby | |
| 2001/0037219 A1 | 11/2001 | Malik | |
| 2002/0010679 A1 | 1/2002 | Felsher | |
| 2002/0012526 A1 | 1/2002 | Sai | |
| 2002/0022975 A1 | 2/2002 | Blasingame | |
| 2002/0026329 A1 | 2/2002 | Saito | |
| 2002/0029157 A1 | 3/2002 | Marchosky | |
| 2002/0035486 A1 | 3/2002 | Huyn | |
| 2002/0062225 A1 | 5/2002 | Siperco | |
| 2002/0078044 A1 | 6/2002 | Song | |
| 2002/0082865 A1 | 6/2002 | Bianco | |
| 2002/0116188 A1 | 8/2002 | Amir | |
| 2002/0138271 A1 | 9/2002 | Shaw | |
| 2002/0145742 A1 | 10/2002 | Koenig et al. | |
| 2003/0115054 A1 | 6/2003 | Iso-Sipila | |
| 2003/0135095 A1 | 7/2003 | Iliff | |
| 2003/0140044 A1 | 7/2003 | Mok | |
| 2004/0034869 A1 | 2/2004 | Wallace | |
| 2004/0059599 A1 | 3/2004 | McIvor | |
| 2004/0133560 A1 | 7/2004 | Simske | |
| 2004/0153289 A1 | 8/2004 | Casey | |
| 2004/0243443 A1 | 12/2004 | Asano | |
| 2005/0055399 A1 | 3/2005 | Savchuk | |
| 2005/0096906 A1 | 5/2005 | Barzilay | |
| 2005/0137723 A1 | 6/2005 | Liu | |
| 2005/0147214 A1 | 7/2005 | Goerg et al. | |
| 2005/0149569 A1 | 7/2005 | Hariharan et al. | |
| 2005/0165626 A1 | 7/2005 | Karpf | |
| 2005/0172022 A1 | 8/2005 | Brown | |
| 2006/0001666 A1 | 1/2006 | Cake et al. | |
| 2006/0011399 A1 | 1/2006 | Brockway et al. | |
| 2006/0028556 A1 | 2/2006 | Bunn | |
| 2006/0047497 A1 | 3/2006 | Chen | |
| 2006/0052674 A1 | 3/2006 | Eisenstein | |
| 2006/0053009 A1 | 3/2006 | Jeong | |
| 2006/0085347 A1 | 4/2006 | Yiachos | |
| 2006/0148528 A1 | 7/2006 | Jung | |
| 2006/0253281 A1 | 11/2006 | Letzt | |
| 2006/0293891 A1 | 12/2006 | Pathuel | |
| 2007/0024454 A1 | 2/2007 | Singhal | |
| 2007/0074114 A1 | 3/2007 | Adjali | |
| 2007/0124135 A1 | 5/2007 | Schultz | |
| 2007/0168413 A1 | 7/2007 | Barletta | |
| 2007/0208800 A1 | 9/2007 | Frohlich | |
| 2007/0216708 A1 | 9/2007 | Mackay | |
| 2007/0276270 A1 | 11/2007 | Tran | |
| 2008/0040151 A1 | 2/2008 | Moore | |
| 2008/0066973 A1 | 3/2008 | Furuki | |
| 2008/0104048 A1 | 5/2008 | Surendran | |
| 2008/0126426 A1 | 5/2008 | Manas | |
| 2008/0133233 A1 | 6/2008 | Tsubura | |
| 2008/0195495 A1 | 8/2008 | Rubin et al. | |
| 2008/0212746 A1 | 9/2008 | Gupta | |
| 2008/0244453 A1 | 10/2008 | Cafer | |
| 2008/0301176 A1 | 12/2008 | Fanelli et al. | |
| 2008/0303811 A1 | 12/2008 | Van Luchene | |
| 2008/0313536 A1 | 12/2008 | Larsen | |
| 2008/0319750 A1 | 12/2008 | Potter | |
| 2009/0055735 A1 | 2/2009 | Zaleski | |
| 2009/0077045 A1 | 3/2009 | Kirchmeier | |

(56) References Cited

U.S. PATENT DOCUMENTS

| | | |
|---|---|---|
| 2009/0117922 A1 | 5/2009 | Bell |
| 2009/0292554 A1 | 11/2009 | Schultz |
| 2009/0313347 A1 | 12/2009 | Engel |
| 2010/0036871 A1 | 2/2010 | Beckey et al. |
| 2010/0076333 A9 | 3/2010 | Burton |
| 2010/0169108 A1 | 7/2010 | Karkanias |
| 2010/0228656 A1 | 9/2010 | Wasserblat et al. |
| 2010/0262435 A1 | 10/2010 | Smith |
| 2010/0286490 A1 | 11/2010 | Koverzin |
| 2011/0034565 A1 | 2/2011 | Regan |
| 2011/0040155 A1 | 2/2011 | Guzak |
| 2011/0068934 A1 | 3/2011 | Weng et al. |
| 2011/0091050 A1 | 4/2011 | Hanai |
| 2011/0099189 A1 | 4/2011 | Barraclough |
| 2011/0099490 A1 | 4/2011 | Barraclough |
| 2011/0118555 A1 | 5/2011 | Dhumne |
| 2011/0148668 A1 | 6/2011 | Li |
| 2011/0184781 A1 | 7/2011 | Hussam |
| 2011/0191122 A1 | 8/2011 | Kharraz Tavakol |
| 2011/0202866 A1 | 8/2011 | Huang |
| 2011/0239158 A1 | 9/2011 | Barraclough |
| 2012/0005099 A1 | 1/2012 | Beckey |
| 2012/0112879 A1 | 5/2012 | Ekchian |
| 2012/0198385 A1 | 8/2012 | Audet |
| 2012/0299926 A1 | 11/2012 | Hodes |
| 2012/0306648 A1 | 12/2012 | Karaffa |
| 2012/0306925 A1 | 12/2012 | Hwang |
| 2012/0323589 A1 | 12/2012 | Udani |
| 2012/0323796 A1 | 12/2012 | Udani |
| 2013/0009907 A1 | 1/2013 | Rosenberg |
| 2013/0024206 A1 | 1/2013 | Hughes |
| 2013/0085781 A1 | 4/2013 | Navani |
| 2013/0111331 A1 | 5/2013 | Rosen et al. |
| 2013/0124192 A1 | 5/2013 | Lindmark |
| 2013/0163956 A1 | 6/2013 | Medhurst |
| 2013/0185071 A1 | 7/2013 | Chen |
| 2013/0257777 A1 | 10/2013 | Benko |
| 2013/0275151 A1 | 10/2013 | Moore |
| 2013/0325493 A1 | 12/2013 | Wong |
| 2014/0019119 A1 | 1/2014 | Liu |
| 2014/0068489 A1 | 3/2014 | Wyland |
| 2014/0074454 A1 | 3/2014 | Brown |
| 2014/0081667 A1 | 3/2014 | Joao |
| 2014/0136233 A1 | 5/2014 | Atkinson |
| 2014/0143671 A1 | 5/2014 | Kovalick |
| 2014/0164310 A1 | 6/2014 | Chen |
| 2014/0164784 A1 | 6/2014 | Sinderbrand |
| 2014/0172707 A1 | 6/2014 | Kuntagod |
| 2014/0172804 A1 | 6/2014 | Kaufman |
| 2014/0195221 A1 | 7/2014 | Frank |
| 2014/0244277 A1 | 8/2014 | Krishna |
| 2014/0249860 A1 | 9/2014 | Rynchek |
| 2014/0253467 A1 | 9/2014 | Hicks |
| 2014/0304005 A1 | 10/2014 | Hughes |
| 2014/0304200 A1 | 10/2014 | Wall |
| 2014/0379374 A1 | 12/2014 | Vinals |
| 2015/0038123 A1 | 2/2015 | Tuukkanen |
| 2015/0058013 A1 | 2/2015 | Pakhomov |
| 2015/0072330 A1 | 3/2015 | Rosenberg |
| 2015/0100339 A1 | 4/2015 | Kim |
| 2015/0134346 A1 | 5/2015 | Hyde |
| 2015/0149095 A1 | 5/2015 | Otvos |
| 2015/0164436 A1 | 6/2015 | Maron |
| 2015/0169717 A1 | 6/2015 | Wang |
| 2015/0178457 A1 | 6/2015 | Grimley |
| 2015/0206544 A1 | 7/2015 | Carter |
| 2015/0228277 A1 | 8/2015 | Anhari |
| 2015/0242585 A1 | 8/2015 | Spiegel |
| 2015/0257681 A1 | 9/2015 | Shuster |
| 2015/0258892 A1 | 9/2015 | Wu |
| 2015/0310455 A1 | 10/2015 | Vinals |
| 2015/0314681 A1 | 11/2015 | Riley, Sr. |
| 2015/0363657 A1 | 12/2015 | Shigemura |
| 2015/0379200 A1 | 12/2015 | Gifford |
| 2016/0004820 A1 | 1/2016 | Moore |
| 2016/0012196 A1 | 1/2016 | Mark |
| 2016/0027264 A1 | 1/2016 | Choi |
| 2016/0078771 A1 | 3/2016 | Zhuang |
| 2016/0080403 A1 | 3/2016 | Cunningham |
| 2016/0143594 A1 | 5/2016 | Moorman |
| 2016/0297359 A1 | 10/2016 | Kirsch et al. |
| 2016/0342741 A1 | 11/2016 | Chin |
| 2017/0007167 A1 | 1/2017 | Kostic et al. |
| 2017/0060997 A1 | 3/2017 | Lee |
| 2017/0161439 A1 | 6/2017 | Raduchel |
| 2017/0166054 A1 | 6/2017 | Ayala Rodriguez |
| 2017/0190251 A1 | 7/2017 | Wu |
| 2017/0195637 A1 | 7/2017 | Kusens |
| 2017/0200449 A1 | 7/2017 | Penilla et al. |
| 2017/0235888 A1 | 8/2017 | Rahman |
| 2017/0251985 A1 | 9/2017 | Howard |
| 2017/0333560 A1 | 11/2017 | Epshtein |
| 2017/0359551 A1 | 12/2017 | Shaw |
| 2018/0027006 A1 | 1/2018 | Zimmermann |
| 2018/0032997 A1 | 2/2018 | Gordon |
| 2018/0060899 A1 | 3/2018 | Das |
| 2018/0090155 A1 | 3/2018 | Moriya |
| 2018/0144763 A1 | 5/2018 | Khaleghi |
| 2018/0153862 A1 | 6/2018 | Coric |
| 2018/0193652 A1 | 7/2018 | Srivastava |
| 2018/0200142 A1 | 7/2018 | Freeman |
| 2018/0211059 A1 | 7/2018 | Aunger |
| 2018/0214061 A1 | 8/2018 | Knoth |
| 2018/0267700 A1 | 9/2018 | Kaditz |
| 2018/0285542 A1 | 10/2018 | Xiao |
| 2018/0322265 A1 | 11/2018 | Kwok-Suzuki et al. |
| 2019/0006040 A1 | 1/2019 | Fleming |
| 2019/0035132 A1 | 1/2019 | Dirksen |
| 2019/0051144 A1 | 2/2019 | David |
| 2019/0060367 A1 | 2/2019 | Zhang |
| 2019/0095632 A1 | 3/2019 | Seinen |
| 2019/0155954 A1 | 5/2019 | Goyal |
| 2019/0239789 A1 | 8/2019 | Jung |

OTHER PUBLICATIONS

Matheson, "Watch Your Tone—Voice-Analytics Software Helps Customer-Service Reps Build Better Rapport with Customers," MIT News Office, http://news.mit.edu/2016/startup-cogito-voice-analytics-call-centers-ptsd-0120; Jan. 20, 2016; 4 pages.

Mullin, "Rewriting Life—Voice Analysis Tech Could Diagnose Disease," https://www.technologyreview.com/s/603200/voice-analysis-tech-could-diagnose-disease/; Jan. 19, 2017; 9 pages.

Nield, "Scientists Can Now Diagnose Depression Just by Listening to Your Voice," IEEE Transactions on Affective Computing; Science Alert, https://www.sciencealert.com/this-computer-program-can-tell-when-someone-s-depressed-by-their-speech-patterns; Jul. 11, 2016; 4 pages.

PCT International Search Report and Written Opinion, regarding International Application No. PCT/US2020/017781 dated Jun. 2, 2020, 12 pages.

PCT International Search Report and Written Opinion, regarding International Application No. PCT/US2019/019438, dated Jun. 14, 2019, 19 pages.

Scherer et al., "Investigating Voice Quality as a Speaker-Independent Indicator of Depression and PTSD", University of Southern California, Institute for Creative Technologies; 5 pages; Los Angeles, California, 2013.

Shah, Bhakti, "eClinicalWorks Invest $25 Million in Patient Engagement," dated Feb. 6, 2013, 3 pages—https://www.eclinicalworks.com/pr-eclinicalworks-invests-25-million/.

* cited by examiner

HEALTH MONITORING SYSTEM AND APPLIANCE

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND OF THE INVENTION

Field of the Invention

This document relates to systems and techniques for electronic appliances, speech analysis and recognition, and image analysis and recognition.

Description of the Related Art

Conventional techniques for determining a patient status often fail to provide timely medical intervention.

SUMMARY

The following presents a simplified summary of one or more aspects in order to provide a basic understanding of such aspects. This summary is not an extensive overview of all contemplated aspects, and is intended to neither identify key or critical elements of all aspects nor delineate the scope of any or all aspects. Its sole purpose is to present some concepts of one or more aspects in a simplified form as a prelude to the more detailed description that is presented later.

This document describes systems, processes and techniques that may be used to manage and process the recording, arrangement, text processing, word recognition, and/or review of information optionally for or in an electronic notebook such as a patient, psychiatrist, psychologist, or other medical professional electronic notebook.

An aspect of this disclosure relates to analyzing speech patterns and content to identify potential medical condition. An aspect of this disclosure relates to analyzing facial expressions to identifying health status medical conditions.

An aspect to this disclosure relates to converting audible expressions of a user, such as a patient, to text, and to identifying audible expressions that cannot be translated to words. An aspect of this disclosure relates to identifying the length of pauses between and/or during audible expressions. An aspect of this disclosure relates to identifying the velocity of audible expressions. An aspect of this disclosure relates to identifying changes of topics in the audible expressions. An aspect of this disclosure relates to determining the rapidity in changes in topics. An aspect of this disclosure relates to analyzing a power and/or magnitude spectrum corresponding to a user's speech to detect vocal track leaks, improper onsets and offsets of stop and affricate closures, vocal tract constrictions within a vowel segment, levels and increases in jitter (glottal cycle lengths) and shimmer, pitch and variations in pitch and/or pitch period, volume levels, intakes of air, and/or other indications of vocal tract formation and muscle control, which may indicate health issues. An aspect of this disclosure relates to identifying repetitive speech. An aspect of this disclosure relates to identifying disconnected audible expressions.

An aspect of this disclosure relates to categorizing audible expressions and/or facial expressions as indicating or failing to indicate a potential medical condition. An aspect of this disclosure related to generating alerts based at least in part on such categorizations. An aspect of this disclosure relates to determining whether a medical intervention is needed. An aspect of this disclosure relates to causing a medical treatment to be applied.

An aspect of this disclosure relates to an electronic device configured to process audible expressions from users, comprising: a network interface; at least one computing device; computer readable memory including instructions operable to be executed by the at least one computing device to perform a set of actions, configuring the at least one computing device: receive in real time, over a network via the network interface, a digitized human vocal expression of a first user and one or more digital images from a remote device; process the received digitized human vocal expression to determine characteristics of the human vocal expression, including: determine, using a pitch analysis module, a pitch of the human vocal expression; determine, using a volume analysis module a volume of the human vocal expression; determine, using a rapidity analysis module how rapidly the first user is speaking in the human vocal expression; determine, using a vocal tract analysis module, a magnitude spectrum of the human vocal expression; identify, using a non-speech analysis module, pauses in speech in the human vocal expression; use a natural language module to convert audible speech in the human vocal expression to text and to understand audible speech in the human vocal expression; compare the determined characteristics of the human vocal expression with baseline, historical characteristics of human vocal expressions associated with the first user to identify changes in human vocal expression characteristics of the first user; process the received one or more images to detect characteristics of the first user face, including detecting if one or more of the following are present: a sagging lip, a crooked smile, uneven eyebrows, facial droop; compare the detected characteristics of the first user face with baseline, historical characteristics of the first user face accessed from a data store, and identify changes in characteristics of the first user face; based at least on part on identified changes in human vocal expression characteristics of the first user and identified changes in characteristics of the first user face, determine if a vehicle is to be deployed to the first user; and at least partly in response to a determination that a vehicle is to be deployed to the first user, enable a vehicle to be deployed to a location of the first user.

An aspect of this disclosure relates to an electronic device, comprising: a network interface; at least one computing device; computer readable memory including instructions operable to be executed by the at least one computing device to perform a set of actions, configuring the at least one computing device: receive, over a network via the network interface, a digitized human vocal expression of a first user; convert at least a portion of the digitized human vocal expression to text; process the received digitized human vocal expression to determine characteristics of the human vocal expression, including: determine a pitch of the human vocal expression; determine a volume of the human vocal expression; determine how rapidly the first user is speaking in the human vocal expression; determine a magnitude and/or power spectrum of the human vocal expression; determine pauses in speech in the human vocal expression; analyze lexicon usage, syntax, semantics, and/or discourse patterns in speech in the human vocal expression; compare the determined characteristics of the human vocal expression with baseline, historical characteristics of human vocal expressions associated with the first user to identify changes in human vocal expression characteristics of the first user; based at least on part on the comparison, determine if a first action is to be taken.

An aspect of this disclosure relates to a computer implemented method, comprising: receiving a digitized human vocal expression of a first user from a first user device; converting at least a portion of the digitized human vocal expression to text; processing the received digitized human vocal expression to determine characteristics of the human vocal expression, including: determining a pitch of the human vocal expression; determining a volume of the human vocal expression; determining how rapidly the first user is speaking in the human vocal expression; determining a magnitude and/or power spectrum of the human vocal expression; determining pauses in speech in the human vocal expression; analyzing lexicon usage, syntax, semantics, and/or discourse patterns in speech in the human vocal expression; comparing one or more of the determined characteristics of the human vocal expression with one or more baseline, historical characteristics of human vocal expressions associated with the first user; based at least on the comparison, determining if a first action is to be taken.

An aspect of this disclosure relates to a computer implemented method, comprising: receiving, at a computerized device, a digitized human vocal expression of a first user; processing the received digitized human vocal expression to determine characteristics of the human vocal expression, including: determining a volume of the human vocal expression; determining how rapidly the first user is speaking in the human vocal expression; generating spectrum analysis of the human vocal expression; determining pauses in speech in the human vocal expression; analyzing lexicon usage, syntax, semantics, and/or discourse patterns in speech in the human vocal expression; comparing one or more of the determined characteristics of the human vocal expression with one or more baseline, historical characteristics of human vocal expressions associated with the first user; based at least on part on the comparison, determining if a first action is to be taken.

BRIEF DESCRIPTION OF THE DRAWINGS

Embodiments will now be described with reference to the drawings summarized below. These drawings and the associated description are provided to illustrate example aspects of the disclosure, and not to limit the scope of the invention.

DETAILED DESCRIPTION

Figure 1:
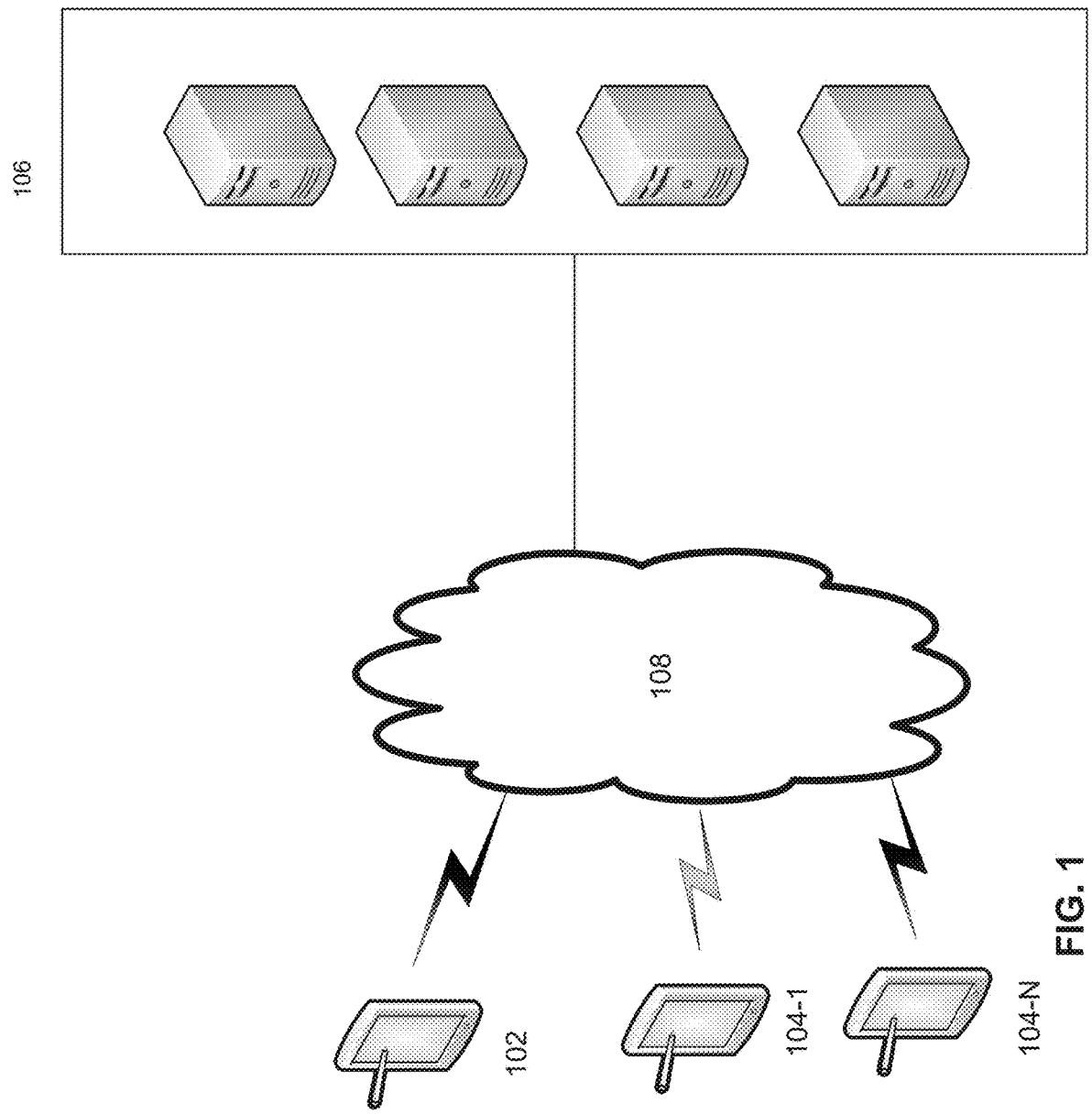
FIG. 1 illustrates an example architecture.

This document describes systems, processes, and techniques that may be used to process the recording of audible expressions from a user (e.g., a patient), the conversion of audible expressions into phonemes and text (word recognition), and/or the identification of audible expressions that indicate an adverse medical condition. This document also describes systems, processes and techniques that may be used to process the recording of images of a user (e.g., a patient), extract features of the user, and the identification of features that indicate an adverse medical condition. An electronic notebook may be utilized in conjunction with such systems, processes and techniques.

The disclosed processes may be performed in whole or in part by a user device and/or a cloud-based system. For example, some or all of a given disclosed process may be executed by a secure, cloud based system comprised of co-located and/or geographically distributed server systems. Information may be received by the cloud-based system from one or more user terminals (e.g., via a desktop computer, laptop computer, tablet, smart phone, networked television, network connected wearable device, a vehicle (e.g., equipped with a microphone, camera, display, and wireless network radio), dangerous machinery (e.g., equipped with a microphone, camera, display, and wireless network radio), or the like).

By way of illustration, optionally a given user terminal may communicate patient information (e.g., audible and/or textual expressions, images, biometrics, etc.) from and/or to the cloud-based system via a web document using a browser and/or via a dedicated application (sometimes referred to herein as an "app") installed and hosted on a user terminal.

Thus, optionally, some or all of the information processing described herein may be performed via a system remote from a user terminal (e.g., by the cloud system), or optionally some or all of the information processing described herein may be performed by the user terminal.

Optionally, users may comprise one or more medical professionals (e.g., a psychiatrist, a family physician, a neurologist, a geriatrician, a therapist, etc.), patients, patient family members, patient caretakers, and/or the like.

As will be described in greater detail herein, a speech recognition engine that employs natural language processing (sometimes referred to as computational linguistics) may be utilized to analyze and/or understand audible speech of a user. The speech recognition engine may be speaker independent.

Certain background information will now be provided related to speech. Words are expressed as combinations of basic speech sounds, sometimes referred to as phonemes. Phonemes may be classified into vowels and consonants. Such classification may be based on differences in phoneme waveforms and vocalization techniques. Vowels are articulated by arranging a speaker's vocal anatomy into relatively fixed configurations and blowing air across the speaker's vocal cords. As the cords vibrate, a train of air impulses is injected into the vocal tract, resonating at specific frequencies. The articulation of vowels does not result in significant obstruction of the airstream, and the sagittal midline of the vocal tract remains open. Because of cord vibration, the waveforms of vowels show periodic behavior, with a basic waveform repeating at a rate referred to as a pitch period.

Consonants, on the other hand, are formed by forming constrictions in the vocal tract using the tongue and other muscles, and obstructing the airflow using teeth, lips or tongue, causing momentary pauses in the speech signal, and then expelling air. Consonants may include a glottal stop, oral-nasal contrasts, affricates, fricatives, and constriction occurring along sagittal midline of the vocal tract. Thus, the waveforms of consonants include short pauses, reflected in dips in the amplitude of the speech signal. Speech that is unvoiced (such as a cough or a breath) does not exhibit periodicity, and this lack of periodicity may be used to distinguish such unvoiced sounds from phonemes.

FIG. 1 illustrates an example architecture. A system 106 (which may be a cloud based system comprising one or more servers that are co-located and/or that are geographically dispersed) may host one or more applications that when executed cause a variety of the processes described herein to execute. For example, the system 106 may include a speech analysis engine, an image analysis engine, and/or an action determination module as described in greater detail herein.

Optionally, the cloud system 106 may include one or more Apache Hadoop clusters, optionally including a Hadoop distributed file system (HDFS) and a Hadoop MapReduce parallel processing framework. The system 106 may be configured to process and store large amounts of data that would not be effectively by conventional system. The system 106 may be configured to process and store large amounts of structured data, unstructured data, and/or semi-structured data. The data may relate to the patient-related data (including sound and/or image (e.g., still or video) recordings, scans, test results, contact information, calendaring information, biographical data, patient-related team data, etc.). The clusters may comprise master nodes (e.g., a name node, a job tracker, etc.), and slave nodes (e.g., data nodes, task trackers, etc.). A given data node serves data over a network using the distributed file system (e.g., HDFS) protocol. The file system may utilize a TCP/IP layer for communication. The distributed file system may store large files across multiple data node machines and may store copies of data on multiple hosts to enhance reliability and data availability.

With respect to the optional Hadoop implementation, other systems may submit tasks to the job tracker, which in turn, distributes the tasks to available task tracker nodes. Optionally, the job tracker may attempt to distribute a given task to a node in geographic proximity to the needed data. While the foregoing example refers to Hadoop clusters and related components, other distributed platforms may optionally be used in addition or instead to process and store data, such as large amounts of data including structured, unstructured, and/or semi-structured data, (e.g., distributed platforms utilizing Bashreduce, Qizmt, Spark, Disco Project, etc.).

The system 106 may communicate over one or more wired and/or wireless local and/or wide area networks (e.g., the Internet) 108 with one or more user terminals, such as one or more patient terminals 102 and one more medical provider or patient team member terminals 104-1 . . . 104-N. A given terminal may optionally be a wireless mobile device (e.g., a smart phone, tablet, laptop, wearable, or the like). A given wireless device may optionally be equipped with one or more wireless interfaces to communicate over WiFi, Bluetooth™, other local area wireless networks, other personal area networks, cellular networks, or the like. The user terminals may optionally be equipped with one or more antennas connected to respective wireless interfaces. The antennas may be located within the housing of the user terminal, and/or on the housing surface of the user terminal. The user terminals may be wired or wireless non-mobile terminals, such as a desktop computer, a fixed or large networked television, a game console, or the like.

The user terminals may include a variety of sensors (e.g., sound, image, orientation, pressure, light, acceleration, and/or other sensors) configured to detect user input and interaction with the user terminals. The user terminals may include touch screens configured to display user interfaces and data and receive user input via touch. The user terminals may include physical keyboards. The user terminals may include one or more microphones to receive voice data and/or commands, and one or more speakers to play audible content. The user terminals may include a camera configured to capture, record, and/or stream video (and/or still image) data (which may be stored or streamed in association with captured audio data) to other systems, such as the system 106. For example, the camera may be a front facing camera of a phone, a PC/laptop webcam, or other image capture device. A given user terminal may include or be configured with media players that enable the user terminal to play video and/or audio content, and display still images.

The user terminals may be associated with various user-types, such as patients and patient "team members" (e.g., family members of patients, patient caretakers, medical personnel, medical facilities, or other members of a support network).

Information between a given user terminal and the system 106 may be synchronized periodically and/or in response to an event (e.g., a detection of a change of data or receipt new data). Optionally, some or all of the information communicated between a user terminal app (e.g., an electronic notebook app used to implement an electronic medical information notebook) and the system 106 are transmitted securely (e.g., to comply with certain regulatory specifications). For example, in order to ensure confidentiality of medication information, the medical information may be handled so as to comply with the Health Insurance Portability and Accountability Act (HIPPA). For example, as discussed below, some or all of the information may be encrypted using an encryption key.

The transmitted data may be secured by establishing a virtual private network (VPN) which establishes an encrypted transmission path between the user terminal and system 106. Optionally, Secure Sockets Layer (SSL), a secure transfer tunnel, may be used to encrypt data in transit between the user terminal (e.g., the notebook app and/or browser) and the system 106. Optionally, some or all of the information may be stored on the user terminal and/or the system 106 using file encryption. Optionally, the encryption key may be stored physically separate from the data being encrypted (e.g., on different physical servers).

Optionally, access to medical and/or other user information (e.g., records of user speech, text, images, test results, diagnosis, etc.) is restricted through user authentication. User authentication may be received in the form of a password and/or biometrics. For example, the user terminal may be equipped with a fingerprint scanner which may be used to compare a fingerprint of someone attempting to access the user terminal and/or the notebook information with that of an authorized user. If there is a match, access may be granted to the user terminal and/or notebook information. If the fingerprint fails to match a reference fingerprint of an authorized user, access to the user terminal and/or notebook information may be denied. Another form of biometrics may be in the form of facial recognition. For example, the user terminal may be equipped with a camera which may be used to capture an image of someone attempting to access the user terminal and/or medical and/or other user information. Features extracted from the image may be compared to stored features of an authorized user. If there is a match, access may be granted to the user terminal and/or user information. If the facial features fail to match, access to the user terminal and/or user information may be denied. Other authentication techniques may be used, such as voice recognition, secure fobs, and the like.

An example of the electronic notebook application will now be described. The electronic notebook may enable two or more users to collaborate over a network. Optionally, a user of the electronic notebook may issue an invitation to one or more other users to collaborate. For example, the collaboration may relate to providing information with respect to a patient (e.g., past or recommended future treatments, changes in the patient's life style, etc.). The invitation may be transmitted from the user's terminal directly to the invitee's terminal, or the invitation may be routed through the remote system to the invitee's terminal. The invitation may be provided to the invitee via a pop-up invitation displayed on the invitee's terminal (e.g., by the notebook app), via an SMS/MMS message, via an email message, via a notebook interface presented via a browser, etc.

A user (who may be a patient, a medical professional, a family member, a caretaker, etc.) may utilize the electronic notebook to record information regarding a patient/client (e.g., a patient with a mental or physical illness, a patient with a physical or cognitive disability, a patient with a drug addiction issue, a patient with aging-related issues, etc.). The notebook may be used to record, process, and reproduce textual information, audio recordings, video recordings (which may include an associated audio recording track), photographs, medical diagnoses, x-rays, MRI scans, CAT scans, PET scans, medical test reports, medical treatment information, and/or other information. For example, textual information may include questions asked by a medical professional of a patient and/or patient's family members, and responses to such questions. Optionally, a given item of information recorded in the notebook may be stored in association with metadata, such some or all of the following an identifier (e.g., name or user ID) associated with the user that recorded the information, an identifier indicating the user function (e.g., psychiatrist, patient, parent of the patient, child of the patient, etc.), geo-location information indicating the physical location of the user when the user entered in the information (e.g., GPS location information received from the user terminal, such as a mobile phone), etc.

By way of example, the electronic notebook may be utilized to record what trigged a visit to an emergency room, which medical professional a patient first encountered when admitted to an emergency room, other medical professionals the patient was treated by in the emergency room, who performed which tests (e.g., x-rays, MRI, other scans, blood tests, etc.). By way of further example, the electronic notebook may be used to list potential diagnoses (e.g., generated by the system as described elsewhere herein or determined by a medical service provider), and to indicate when a given listed diagnosis has been determined to be no longer a potential diagnoses.

The notebook may provide a user interface enabling a team to be specified for a user/patient. For example, that user interface may include a field that specifies who is in charge of monitoring the patient's health generally and/or a specific specified treatment plan. By way of illustration, a physician (including name and specialty) can be specified, a family member (including name and relationship) can be specified, a treatment professional (including name and specialty) can be specified, etc. Other fields may enable a user to specify (e.g., by name, contact information (e.g., email address, SMS address, etc.), or otherwise) which users are to receive a given type of notification. For example, a first set of users may be designated to receive notifications if a patient failed to show up to an appointment, a second set of users may be designated to receive notifications if a patient failed to follow a treatment plan, a third set of users may be designated to receive notifications if it is determined (e.g., based on speech and/or image information) that the patient's detected health status requires urgent attention, and a fourth set of users may be designated to receive notifications if it is determined (e.g., based on speech and/or image information) that the patient's detected health status necessitates an appointment be scheduled for the patient for further evaluation/tests. Users may be included in more than one set. Thus, notifications, such as those discussed herein, may be transmitted to the corresponding set(s) of users designated via the user interface to receive such notifications.

The notebook may also be used to search for and/or display specialists of a specified type that are in the geographic area of the patient (e.g., within a specified region, city, zip code, a specific number of miles from the patient's residence and/or from the device hosting the notebook, etc.). For example, a search for specialists of a specified type that are in the geographic area of the patient may be executed by a search engine which will return a list of names that satisfy the search criteria. The specialist's name may be presented by the notebook app (or a browser) in the form of a link or in association with a link, wherein if the user clicks on the link, the notebook will access and display additional information regarding the specialist, such as the schools attended, the hospitals where the specialist interned, the hospitals where the specialist had a fellowship, the hospitals that the specialist has admission privileges for, rating from one or more rating sources, etc.

The electronic medical information notebook may be configured to make it easy for a patient or patient caretaker to access and understand the medical information, and to enter information, as well as appointments, records, and to do lists. The electronic notebook may include user interfaces configured to receive background and biographical information for a patient, enable the recording of verbal discussions at an appointment, the enable the conversion of voice-to-text, enable the determination or inference of a potential health status of the patient, enable potential diagnoses to be generated, enable notifications to be generated and transmitted, enable medical devices to be controlled (e.g., insulin pump, cardioverter defibrillator, pacemaker, bladder control device, etc.), and the like. For example, a medical device in the inactive state may be activated in response to a detected or inferred health status.

The electronic medical information notebook may further enable the patient or other user to generate lists of questions that are to be asked at an appointment, enable the patient or other user to transmit the list of questions to one or more recipients prior to the appointment, the ability to record referral information, the ability to receive and record contact information, enable the patient or other user to record office visit notes, enable the patient or other user to share information from the notebook with others, enable the patient or other user to record treatment plan information, enable the patient or other user to record medication and prescription information, enable the patient or other user to record medical procedure information, enable the patient or other user to record a diary/chronology of appointments, interventions, testing, etc., enable the patient or other user to combine the diary with collected biographical, medical and clinical information, enable the patient or other user to communicate with medical professionals (e.g., for the purposes of providing check-in information via video conferencing or messaging, text chats, VoIP, or otherwise), enable the patient or other user to receive updates relevant to a user's area of concern, enable the patient or other user to record, track, and analyze medical insurance related matters, enable the patient or other user to search for and access resources by diagnosis, and/or enable the patient or other user to calendar events, such as medical appointments.

For example, when a user initially accesses the electronic notebook application to generate a new electronic notebook, the electronic notebook application may provide a user interface listing various medically-related conditions or categories. By way of non-limiting example, the conditions may include one or more of the following:
  Autistic Spectrum Disorders
  Developmental Disorders
  Learning Disorders
  Emotional or Psychiatric Disorders
  Aging
  Life Altering Illness (e.g., cancer, Parkinson's, ALS)
  Neurological Disorders
  Other Optionally, handwritten entries provided via handwritten touch entry (e.g., via a stylus or user finger/digit) may be analyzed to identify user stress. For example, the smoothness or jaggedness of the handwritten entry may be identified (e.g., by identifying discontinuities or abrupt horizontal inputs followed immediately by abrupt vertical inputs) to infer whether the user is undergoing stress. Similarly, stylus/finger pressure and inclination information may be received (e.g., via a wireless interface), stored and analyzed to identify user stress (e.g., pressure or inclination angle above a respective threshold may indicate stress).

The electronic notebook may include fields for receiving content and/or demographic information of a patient. For example, the fields may include name, address, biological gender, gender identification, date of birth, and/or diagnosis. Other example fields include fields configured to receive an indication as to whether the patient is a primary user of the electronic notebook, and if not, an indication/name as to who is the primary user of the notebook, and the primary user's relationship to the patient (e.g., parent, child, sibling, caretaker, physician, etc.). Still other example fields may include a field to receive an identification as to who is living with the patient and their relationship to the patient (e.g., parent, child, sibling, caretaker, friend, etc.), an identification as to who attends to the patient on a daily or regular basis, an indication as to whether there are family members or staff that assist with the patient, etc.

The electronic notebook diary may be updated (e.g., via voice entry, a keyboard, stylus, or using information recorded via another section of the notebook) with each new appointment, intervention, test, detected medical status, notification, other information discussed herein, etc. Optionally, the diary will sequentially present dates on which an event occurred, and brief description of the event (e.g., "possible stroke detected," "possible PTSD episode detected," "health status alert transmitted to [list of recipients]," "appointment with neurologist", "prescription of Felodipine to control blood pressure," "MRI scan", etc.). Optionally, an additional information control (e.g., a "more" control) may be provided which when activated by a user will cause additional information regarding the event to be accessed and displayed. For example, the additional information may be accessed from another notebook section. By way of illustration, the information may be accessed from an office visit section, a treatment plan section, a medication section, a clinical/therapeutic treatment section, and/or other section. There may be separate diaries for different on-going health concerns.

Optionally, a health timeline may be generated. The health timeline may include some or all of the biographical information collected by the application and/or all some or all of the information from the diary. The health timeline may be utilized to help provide an overview of the patient's issues and potential relationships between such biographical information and the patient's medical issues and/or treatment. Thus, the health timeline may provide a quick overview of the patient and the patient's medical history.

The electronic notebook may optionally include instructions with respect to voice recording appointments and regarding preparing questions for the appointment.

The electronic notebook may optionally include fields of user and/or patient questions for the medical service provider. Thus, such questions may be entered prior to the appointment, avoiding reliance on fallible memory with respect to questions or areas of concerns.

The electronic notebook may include a record control, which when activated, enables video and/or audio to be recorded (e.g., of a given appointment or for patient communications while at home or elsewhere) by the device hosting or accessing the application. For example, the recorded content of the appointment enables the user, patient, and/or other medical professionals to later review the recorded appointment without requiring that the user, patient, and/or other medical professional manually write or type in notes during the appointment. The recording of an appointment will reduce user and/or patient stress during the appointment as there will be no need to manually take notes. For example, because the recorded appointment may include information on new or existing treatment modes (e.g., medication, exercise, physical therapy, et.), the electronic notebook can generate and/or provide user interfaces textually providing such information, and may further generate and/or provide follow-up user interfaces that can be used to receive and record follow-up information indicating whether the patient is taking the medication, following other instructions provided by the doctor/specialist, the patient's physical condition and health, etc.

A given user of the electronic notebook application may establish an account on the cloud system. The user may be asked to provide various items of data during and/or after account setup, which may be stored in the cloud system and/or on the patient's terminal in a user account record. For example, if the user is a patient, during account setup the user may be asked to provide patient history, patient demographics, patient medical service provider information (e.g., names, contact information, specialty, and/or the like), information regarding other members of the patient's support team (e.g., names, contact information, relationship, and/or the like), and/or other patient information discussed herein. The user may also be prompted to enable location based services for the notebook application (e.g., the user may be navigated to a user interface via which the user may enable location based services for the application). This enables the notebook application and/or cloud-based system to access location information (e.g., GPS information, WiFi information, etc.) provided by the user terminal. The location information may be utilized as described elsewhere herein (e.g., to dispatch emergency medical services, transportation, etc.).

The patient may also be asked to make a video and/or audio recording of the patient speaking/vocalizing certain phonemes, vowels, consonants, phrases, sentences, paragraphs, and/or other units of speech. Text (e.g., a script) corresponding to the units of speech may be transmitted for presentation on the patient terminal while the patient is making the recording to enable the patient to read and repeat the presented units of speech text. For example, a user interface may present the recording in real time in a first area of the patient terminal display, and at the same time may present units of speech text (e.g., a script) in second area of the patient terminal display. The user may optionally be instructed to read certain items of text at a normal rate, certain items of text at a slow rate, and certain items of text at a rapid rate. The user may optionally be instructed to read certain items of text at a normal volume, certain items of text at a high volume, and certain items of text at a low volume.

The patient may also be prompted to provide free form speech, optionally regarding one or more specified topics and without a script. The free form speech may indicate the patient's current lexicon usage, syntax, semantics, and/or discourse patterns.

The video and/or audio recording of the patient may be used as a baseline for determining at a later time if the patient's health status has changed or is unchanged, as discussed elsewhere herein. The notebook application may periodically (e.g., once a day, twice a day, once a week, once a month, once every 4 weeks, once every six months, etc.) and/or in response to certain events (e.g., a change in medication, a change in medical status, a change in medical stability, a doctor's appointment, a medical test, and/or other events described herein), prompt the patient to record another baseline of the user speaking certain units of speech and/or free form speech, optionally with accompanying images (e.g., video). The script presented to the patient for the recording may be configured to facilitate the later detection of changes formation of phonemes, pitch, volume, and/or rapidity of speech.

As similarly described elsewhere herein, if at a later time certain changes in the patient's vocalization and/or facial characteristics have been detected, an alert may be generated and transmitted to one or more destinations (e.g., to one or more designated members of the patient's support team, emergency transportation, emergency medical personnel, and/or the like).

Aspects and non-limiting examples of the electronic notebook are described in U.S. Pat. No. 9,899,038, issued Feb. 20, 2018, the content of which is incorporated by reference herein in its entirety.

Figure 2:
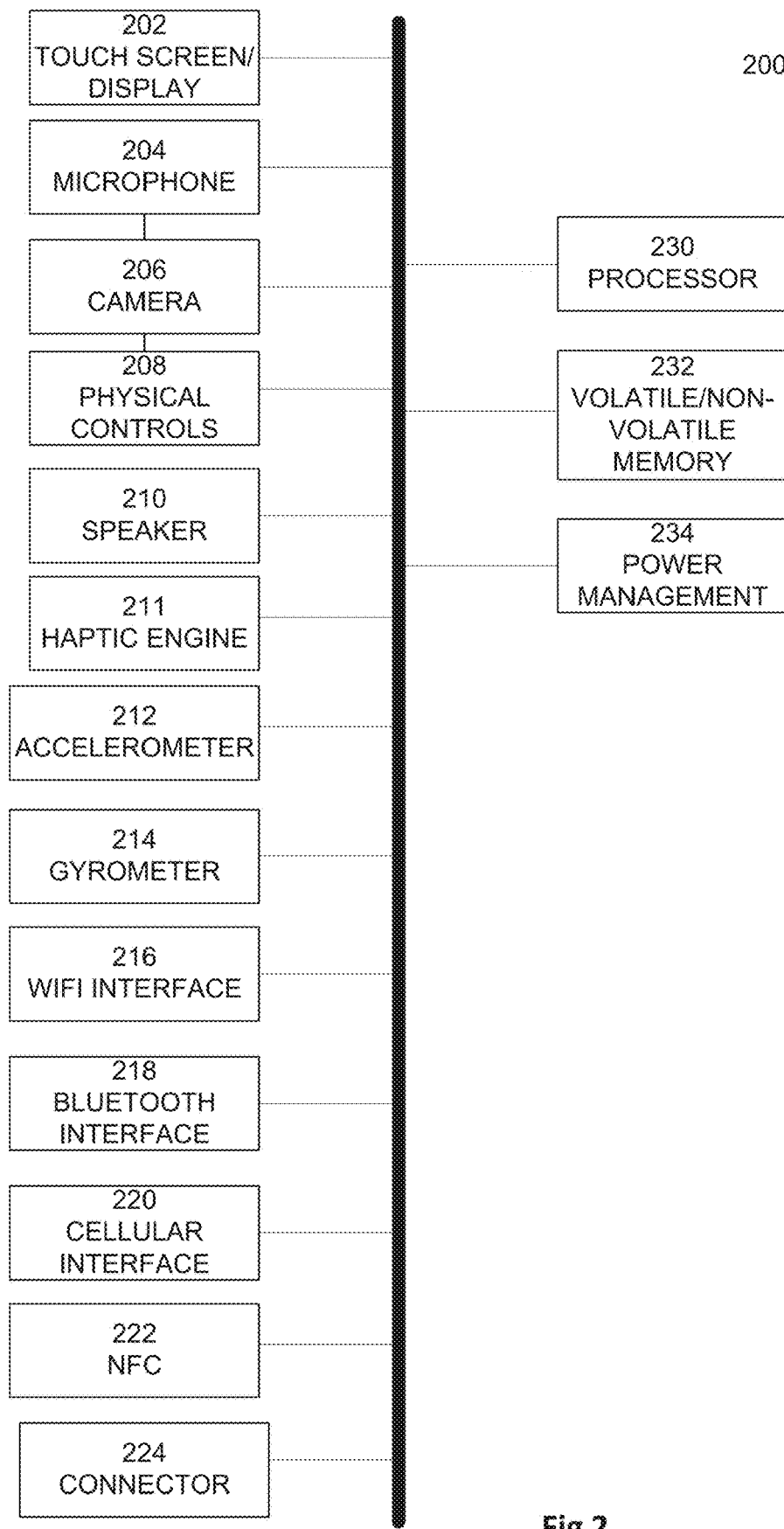
FIG. 2 illustrates an example user terminal architecture.

FIG. 2 illustrates an example user terminal 200 in the form of a tablet, phone, laptop, or appliance. In the example illustrated in FIG. 2, the user terminal 200 includes various user input/output devices, such as a touchscreen/display 202, a microphone 204, a camera 206, physical controls 208 (e.g., a power on/off control, a volume control, a home control, etc.), a speaker 210, and/or other user input/output devices. The user terminal 200 may optionally include a haptic engine 211 that provides kinesthetic communication to the user (e.g., via vibrations or taps, which may be used to confirm a user input or to provide a notification), an accelerometer 212 that measures acceleration in 2-3 directions, and/or a gyrometer (e.g., a 3-axis gyroscope) 214 that measures orientation in three axis. The user terminal 200 may be equipped with an external or integral physical keyboard, trackpad, joystick, electronic pen, and/or other input device.

The user terminal 200 may include one or more wireless and/or wired interfaces. For example, the user terminal 200 may include a WiFi interface 216, a Bluetooth interface 218, a cellular interface 220, an NFC (near field communication) interface 222, and/or one or more physical connectors 224 (e.g., a USB connector, a LIGHTING connector, and/or other connector). The user terminal 200 further comprises a processor device (e.g., a microprocessor) 230, volatile memory (e.g., RAM solid state memory) and non-volatile memory (e.g., FLASH memory), and a power management device 234.

An application (e.g., an electronic notebook application) may be utilized to transmit audible input received from a user (e.g., a patient) via the microphone 204 and digitized using an analog-to-digital converter over a network to the system 106. Optionally, the audible input analysis may be performed using the voice-text application 306 discussed with reference to FIG. 3. The audible input may be initiated by the user or may be provided in response to a textual or audible prompt provided using the notebook application. As described herein, the system 106 may optionally analyze the audible input (e.g., to determine a user's health status), and based on the audible input, take an appropriate action.

An application (e.g., the electronic notebook application) may also be utilized to transmit image data received by the camera 206 over a network to the system 106. The user terminal 200 may transmit the image data over a network to the system 106 for processing and analysis (e.g., to determine a user's health status) as described elsewhere herein, and based on the image data, take an appropriate action. The action may be recorded in the notebook app diary and/or health timeline with a timestamp.

The electronic notebook application may be provided or accessed in the form of any application obtained/downloaded by the user terminal 200 via a third party application store and/or via the system 106.

The electronic notebook user interfaces may include a variety of data entry fields. The fields may be populated via a keyboard, a stylus, via voice entry (provided via the microphone 204) which may be converted to text via a voice-to-text module, or via facial, limb, or figure gestures captured by the camera 206. The keyboard and/or stylus may be included with the user terminal 200. The stylus may optionally be configured with a sensor to determine stylus inclination and/or a sensor to measure the pressure being applied to the stylus by the user. The pressure and inclination information may be transmitted to the user terminal 200 (e.g., via Bluetooth or other wireless or wired protocol) and such information may be used to identify user issues as described elsewhere herein.

Figure 3:
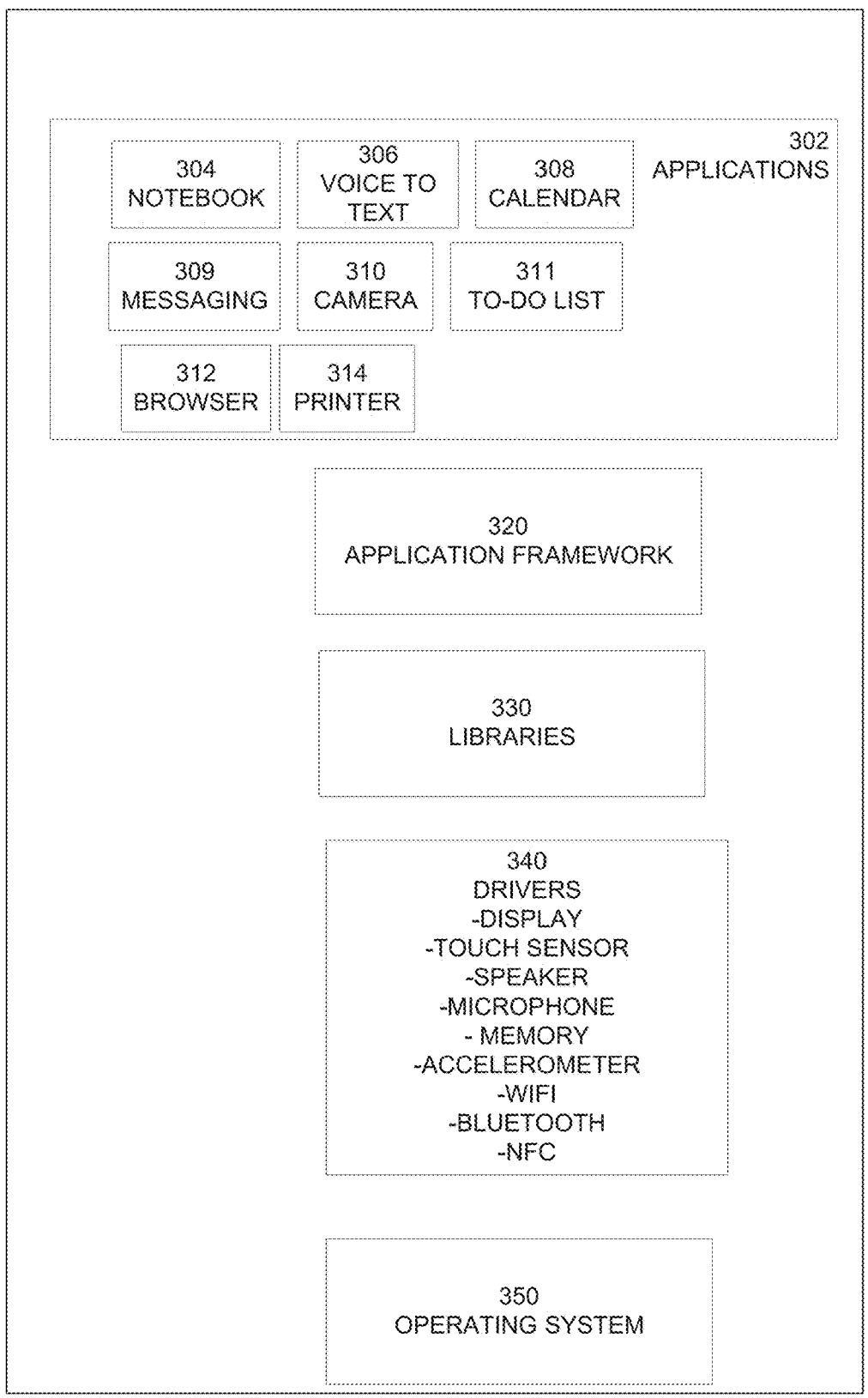
FIG. 3 illustrates an example software architecture for the example user terminal.

FIG. 3 illustrates an example, optional software architecture for a touch-enabled version of the example user terminal 200 illustrated in FIG. 2. The software architecture may include an operating system 350 (e.g., GOOGLE ANDROID, APPLE iOS, MICROSOFT WINDOWS, APPLE OS, UNIX, LINUX, etc.), drivers 340 (e.g., display, touch sensor, speaker, microphone, memory, accelerometer, WiFi, Bluetooth, NFC, etc.), libraries 330 (e.g., SSL, Webkit, SQL, etc.), an application framework 320, and applications 302. For example, the applications 302 may include a notebook application 304, a voice-text application 306, a calendar application 308, a messaging application 309, a camera application 310, a to-do list application 311, a browser application 312, a printer application 314 and/or other applications. A given application may utilize another application as part of its operation. For example, the notebook application 304 may call the voice-text application 306, the calendar application 308, the messaging application 309, the camera application 310, the to-do list application 311, the browser application 312, and/or the printer application 314. Two or more of the applications may be integrated into a single application. The notebook application 304 may be configured to perform some or all of the functions and processes described herein.

Figure 4:
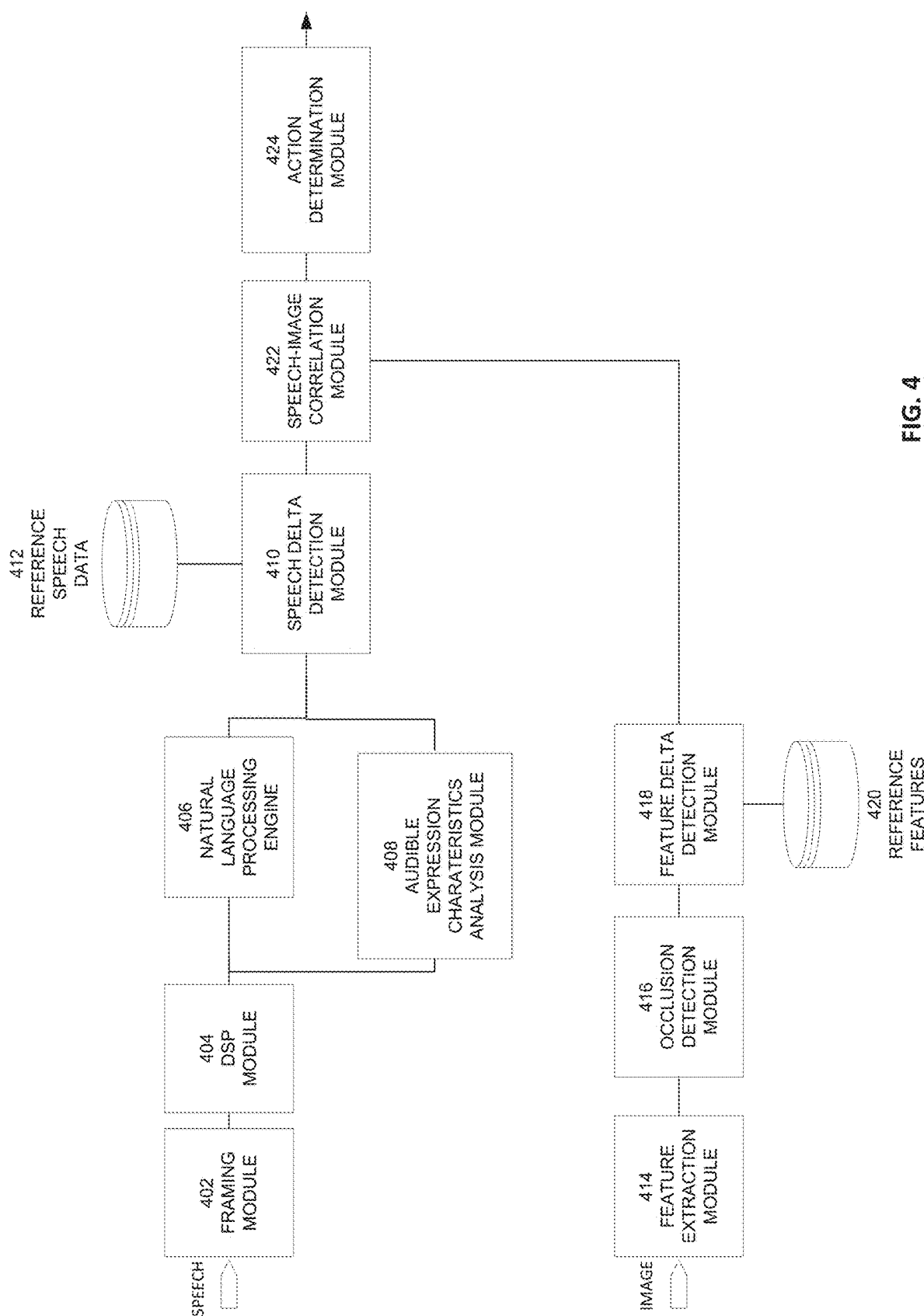
FIG. 4 illustrates an example speech processing system and image processing system.

FIG. 4 illustrates an example speech processing system and image processing system. All of portion of the speech processing system and image processing system may be hosted by the system 106 and/or user terminals (e.g., user terminal 102 or user terminal 104-1). Thus, the speech processing system and image processing system may be a distributed networked system.

For example, the example speech processing system may detect slurred or unintelligible speech, shaky speech, broken speech (where there is a pause within a word), disjointed speech, word interjections, repetitive speech, phrase interjections, sound interjections, word omissions, word revisions, broken suffixes, slower, lower in overall amplitude, errors (at the sentence, word, and/or phonological level), longer vocal tract closure durations than is typically obtained in the analyses of stop consonants, other speech and vocal tract characteristics described herein, and the like. The example speech processing system may detect changes in some or all of the foregoing relative to a baseline or other historical recording.

The comparison of current speech of a user with baseline, historical speech of the same user provides enhanced information as compared to a comparison of current speech of a user with speech of a reference normal population. For example, a comparison of current speech of a user with that of a reference normal population will not indicate changes in a user's medical state or condition. Further, a given user may not be "typical" and hence, a comparison with speech of a reference normal population may provide misleading and erroneous indications with respect to the user's current medical state or condition. However, optionally, a comparison of current speech of a user with that of a reference normal population may be performed and utilized.

A framing module 402 receives digitized audible expressions, in the time domain, from a speaker (e.g., a patient). For example, the audible expressions may have been received via a user terminal microphone (e.g., microphone 204) after having been digitized using an analog-to-digital converter. The digitized audible expressions may be associated with time stamps. A video recording may be made in conjunction with the audio recording, and as discussed below, may also be used to determine changes in the speaker's health status. Optionally, the speaker may be prompted, via a textual script, to speak certain phonemes, vowels, consonants, phrases, sentences, paragraphs, and/or other units of speech. The script may include some or all of the units of speech for which an earlier recording already exits, where the earlier recording may be used as a baseline for comparison. For example, as discussed above, the speaker may have been requested to make a baseline recording of the speaker reading certain units of speech, optionally at different rates and volume levels. The speaker may optionally be prompted to provide free form speech.

If the framing module 402 is hosted by the system 106, the digitized audible expressions may have been transmitted by the user terminal over a network to the system 106. The framing module 402 may apply frame blocking to the digitized audible expression. Frame blocking may be utilized to divide the received audible expression into segments, referred to as frames. For example, a frame may optionally be 5-250 ms in duration (although other durations may be used). A given frame may optionally overlap with a preceding frame (assuming there is a preceding frame) and/or a subsequent frame (assuming there is a subsequent frame). A given frame may be associated with a respective time stamp.

A digital signal processing (DSP) module 404 may optionally be utilized to convert the framed audible expressions from the time domain to the frequency domain. For example, the digital signal processing module 404 may optionally apply a Fast Fourier Transform (FFT) to covert the framed audible expressions from the time domain to the frequency domain and to obtain a magnitude spectrum of the audible expressions. The transformation of speech signals into a spectrum, such as a power and/or magnitude spectrum may make the identification the locations of vowels, consonants, noise, and the like more accurate and may require less processing power to perform such identification. Optionally, frequencies that are close to each other (e.g., within a threshold range) may be warped to a logarithmic scale to reduce the amount of frame data that needs to be processed. Dimensionality reduction can optionally be performed (e.g., using discrete cosine transforms) to further reduce the amount of frame data that needs to be processed. Optionally, a feature vector for a given frame is generated that represents that relative strength of certain frequencies relative to others in the frame (e.g., providing a compact representation of timbre).

A natural language processing engine 406 may be utilized to perform natural language processing on the audible expressions using the output of the DSP module 404. At a high level, the natural language processing engine 406 initially determines the general location of phonemes and their waveform characteristics (e.g., using feature extraction), uses pattern recognition to identify the phonemes, and maps the phonemes onto words. The natural language processing may optionally be speaker independent and/or text independent.

As will be described in greater detail elsewhere herein, the natural language processing engine 406 may be utilized to perform phoneme analysis, lexical analysis, semantic analysis, discourse analysis, and/or pragmatic analysis. The natural language processing engine 406 may optionally identify disjointed speech, repetitive speech, word interjections, phrase interjections, word omissions, word revisions, and/or broken suffixes. The natural language processing engine 406 may output text corresponding to audible expressions and/or generate indications of an estimated/inferred speaker's health status. For example, changes in speech patterns over time (e.g., decreased use of polysyllabic words, decreased average number of words in sentences, increased rate of speech (e.g., hurried/pressured speech)), may indicate new or problematic health issues.

Natural language processing may comprise the utilization of machine learning that analyzes patterns in data to improve the natural language processing software's ability to understand the entry. Natural language processing may utilize sentence segmentation, part-of-speech tagging (e.g., subject, object, modification, noun, adjective, number, etc.), parsing, named entity extraction (e.g., locating and classifying elements in text into various categories such as the names of persons, organizations, locations, expressions of times, quantities, monetary values, percentages, etc.), paraphrase recognition (determining when different phrases or sentences have the same meaning), and/or co-reference resolution (finding all expressions that refer to the same entity in a text).

As will be described in greater detail elsewhere herein, an audible expression characteristics analysis module 408 may be utilized to analysis various audible expression properties, such as pitch, volume, rapidity, vocal tract formation, and non-speech. Detected changes over time (e.g., slurring, air "leaks" during speech, long gaps between words, gaps within words, increases in jitter and shimmer (the frequency and amplitude variation of the sound), etc.) may indicate health issues. For example, jitter corresponds to small fluctuations in glottal cycle lengths and provides an indicator of motor control abilities and the health status of the vocal system.

An optional speech delta detection module 412 accesses historical speech data samples of the speaker from a reference speech database 412, and compares the historical speech data samples with the output of the natural language processing engine 406 and audible expression characteristics analysis module 408 to determine if there has been a material change (which may indicate a change in the speaker's health status). The historical speech data samples may optionally have been recorded as a baseline by the speaker when setting up a notebook account and/or afterwards, as similarly discussed elsewhere herein. Optionally, the historical speech data samples may include samples of the speaker reading a script configured to make it easier to detect changes in speech and vocalizations. Optionally, the historical speech data samples may include free form speech, indicating the speaker's historical, natural lexicon usage, syntax, semantics, and/or discourse patterns.

For example, the speech delta detection module 412 may detect changes in the formation of phonemes, lexicon usage, syntax, semantics, discourse patterns, pitch, volume, rapidity of speech, in inferred vocal tract formation, and in non-speech (e.g., length of pauses between words or other units of speech, shimmer, jitter, coughs, random non-speech audible expressions, etc.). Certain changes may be weighted more heavily than other changes in inferring that there is a change in the speaker's health status. For example, changes in the formation of phonemes (e.g., that indicate slurring of speech) may be weighted more heavily than changes in rapidity of speech.

Optionally, images of the speaker may be analyzed to aid in detecting the speaker's health status. An optional feature extraction module 414 receives digitized image data (e.g., still or video image data) of the speaker (e.g., a patient). For example, the image data may have been received via the user terminal camera (e.g. after having been digitized using an analog-to-digital converter). A given image (e.g., a video frame or still image) may be associated with a time stamp. The image data may have been recorded at the same time as the audible data, as discussed above. If the feature extraction module 414 is hosted by the remote system 106, the digitized image data may have been transmitted by the user terminal over a network to the system 106.

The feature extraction module 414 may extract and analyze features, such as facial features, in the image to perform face and/or emotion classification. For example, the feature extraction module 414 may detect smiles, frowns, sagging lips, crooked smiles, uneven eyebrows, facial droop, and/or other indicators of a health status. By way of illustration, crooked smiles, uneven eyebrows, facial droop on one side of the face, and the like may be indicative of a stroke. An occlusion detection module 416 may identify the occlusion of the speaker's eye(s) by the speaker's eyelids (which may be indicative of a stroke or drug use).

An optional feature delta detection module 418 accesses historical feature data samples of the speaker from a reference features database 420, and compares the historical feature data samples with the outputs of the feature extraction module 414 and the occlusion detection module 416 to determine if there has been a change (which may indicate a change in the speaker's health status). By way of illustration, changes in the speaker's smile, frown, lips (where one side of the user's mouth now droops), eyebrow position, facial droop, etc., may be detected. The historical feature data samples may optionally have been recorded as a baseline by the speaker when setting up a notebook account and/or afterwards, as similarly discussed elsewhere herein. Optionally, the historical feature data samples may include still and/or video images of the speaker reading a script and/or engaging in free form speech.

For example, if the speaker had suffered a stroke (which resulted in facial droop) several weeks ago, and corresponding features were stored in the reference features database 420, then if the current image of the speaker indicates that the speaker has approximately the same facial droop, the feature delta detection module 418 may indicate no change in the speaker's health status. If, on the other hand, the speaker had not previously suffered a stroke (and did not suffer from facial droop), and corresponding "pre-stroke" features were stored in the reference features database 420, then if the current image of the speaker indicates that the speaker now has facial droop, the feature delta detection module 418 may indicate a corresponding change in the speaker's health status (e.g., a stroke).

Certain feature changes may be weighted more heavily than other changes in inferring that there is a change in the speaker's health status. For example, changes in facial droop may be weighted more heavily than changes in eyebrow position in inferring a change in health status.

Optionally, an adverse health status condition may be detected without comparison with historical data (e.g., where applicable speech or image/feature historical data is not available). For example, if slurred speech and facial droop is detected, the system may determine that the user has possibly suffered a stroke (even though the stroke may have occurred months ago).

An optional speech-image correlation module 422 correlates speech data (e.g., the output of the natural language processing engine 406, the audible expression characteristics analysis module 406, and/or the output of the speech delta detection module 410) with image data (e.g., the output of the feature extraction module 414, the occlusion detection module 416, and/or the feature delta detection module 418) using respective time stamps. Such correlations may provide further information on the user's health status. For example, slurring of speech occurring at the same time the speaker's eyelids are occluding more than a certain percentage of the speaker's eyes may indicate a more significant adverse health status than slurring of speech occurring at a different time than eye occlusion.

The action determination module 424 determines what action to take based on the outputs of the natural language processing engine 406, the audible expression characteristics analysis module 406, the output of the speech delta detection module 410, the feature extraction module 414, the occlusion detection module 416, and/or the feature delta detection module 418. For example, the action determination module 424 may access rules from a rules data store that determines what action to take based on the outputs of the natural language processing engine 406, the audible expression characteristics analysis module 406, the output of the speech delta detection module 410, the feature extraction module 414, the occlusion detection module 416, and/or the feature delta detection module 418.

Actions specified by the rules may include generating and transmitting notifications (e.g., via email, text messages, dedicated applications, webpages, or the like) to one or more specified recipients (e.g., a specified patient's referring primary physician, team leader, family members, caretakers, ambulance, etc.), providing instructions to one more medical devices (e.g., insulin pump, cardioverter defibrillator, pacemaker, etc.), dispatching an emergency vehicle, and/or the like. The notification may include location information of the speaker received from the speaker's terminal (e.g., latitude, longitude, an address, etc.), which may be provided by a GPS radio, WiFi localization, or other location determination device or techniques.

A generated notification may include the speech and/or image data that triggered the notification. For example, if the system detects that one side of the speaker's face is drooping in video images and that the speaker is slurring words in audio data, the system may include corresponding video and audio data in the notification, which may be played back via the recipient's receiving terminal and media player. In addition, the notification may include a transcription of the audio data performed by the natural language engine 406, including at least the text (e.g., including keywords) that triggered the notification. The system may identify and highlight in the notification key terms that may indicate a particular cause for concern.

By way of illustration, if the action determination module 424 detects an elevated or immediate need for attention, an alert may be generated and provided to the treating professional (e.g., via a pop-up alert, an SMS/MMS message, an email message, a vibration alert, etc.), where the alert may indicate that the information included in the notification needs to be urgently reviewed, and that the speaker may need immediate attention. For example, words and phrases that indicate urgency (and which may be included and highlighted in the notification) may include some or all of the following terms and/or other terms: numbness, agony, bleeding, broken bone, can't get up, blind, dizzy, hopeless, worthless, suicidal, anxious, depressed, afraid, helpless, afraid, out-of-control, gun, knife, rage, violent, etc.

By way of further example, urgency may be indicated if the speaker's audible expressions is unintelligible or the speech (e.g., slurred speech) or text patterns indicate that the user is engaging in substance abuse (e.g., of drugs or alcohol), suffering a post-traumatic stress disorder (PTSD) episode, or is suffering a stroke. The alert may be dynamically generated and composed to include the keywords/terms that triggered the alert, and/or may indicate that unintelligible/slurred speech was detected. The alert may include historical video and/or audio content for playback so that the recipient can view the change in health status.

Thus, the action determination module 424 may generate or select text, graphics, a score, speech, and/or the like that indicates a recommendation as to how the speaker's detected or inferred health status should be responded to. For example, the recommendation may be one or more of the following:

Scheduling of an appointment with a specified or unspecified health service provider;
Recommend specified testing relevant to the speaker's detected symptoms be performed;
Immediate deployment of an ambulance to bring the speaker to an ambulance;
Asking a neighbor or other person to visit the speaker at the speaker's current location (the location received from the speaker's terminal).

The action determination module 424 may also generate and include in the notification a preliminary diagnosis based on the output of the natural language processing engine 406, the audible expression characteristics analysis module 406, the output of the speech delta detection module 410, the feature extraction module 414, the occlusion detection module 416, and/or the feature delta detection module 418. For example, if slurred speech, facial drooping, and occluded eyes are detected, the rules accessed by the action determination module 424 may indicate that the speaker has undergone a stroke.

Figure 5:
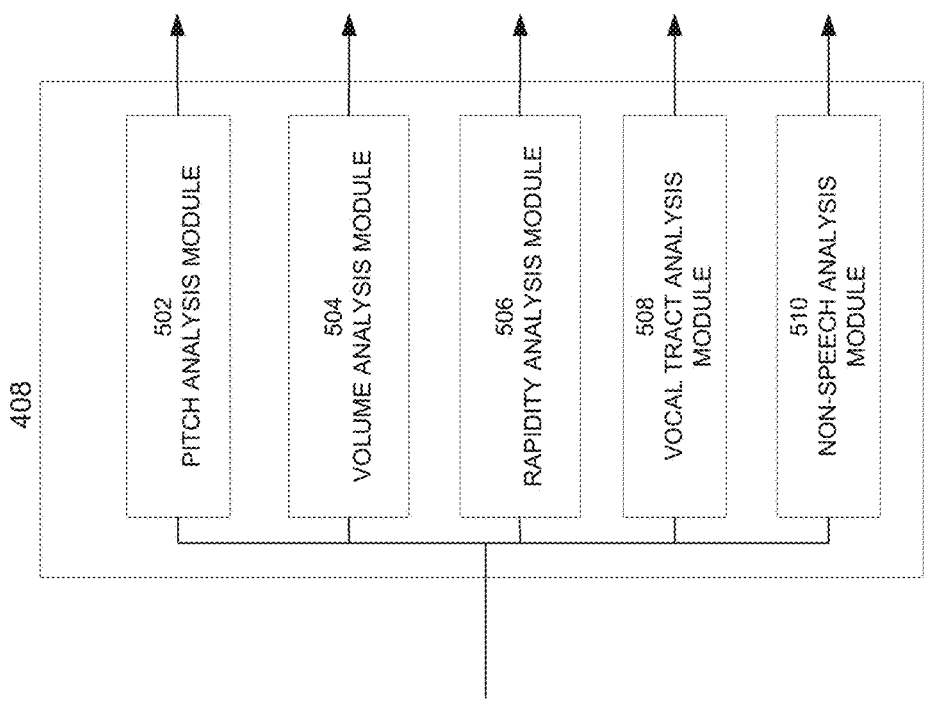
FIG. 5 illustrates an example architecture of an audible expression characteristics analysis module.

FIG. 5 illustrates an example architecture of the audible expression characteristics analysis module 408. A pitch analysis module 502 continuously determines the speaker's pitch. For example, the pitch analysis module 502 may estimate the period of a quasiperiodic signal in the speech, and then invert that value to give the pitch. Optionally, cepstrum pitch determination may be utilized by taking the inverse Fourier transform (IFT) of the logarithm of the estimated spectrum of a signal. A cepstrum indicates the rate of change in spectrum bands. A power cepstrum may be generated by taking the squared magnitude of the inverse Fourier transform of the logarithm of the squared magnitude of the Fourier transform of a signal.

A volume analysis module 502 continuously determines the speaker's speaking volume (e.g., by measuring the overall heights of the peaks in the power spectrum of the speech). A rapidity analysis module 506 may determine how quickly the speaker is speaking by measuring the "quiet time" between words and/or the number of words enunciated over a specified period of time (e.g., 5 seconds, 10 seconds, or other time period). The quiet time may be detected based on the power spectrum, where the overall heights of the peaks in the power spectrum of the speech are below a certain threshold.

A vocal tract analysis module 508 may analyze the magnitude spectrum of the speech to detect air "leaks" from the vocal track during speech (e.g., incomplete closure of the vocal tract which is marked by a "leak" of noise just prior to the fricative portion of a sound), improper onsets and offsets of stop and affricate closures, vocal tract constriction within a vowel segment, levels and increases in jitter (glottal cycle lengths) and shimmer, variations in pitch period when speaking vowels, pitch and variations in pitch, volume levels, intakes of air, and other indications of vocal tract formation and muscle control, which may indicate health issues.

A non-speech analysis module 510 may analyze the speaker's speech for pauses in speech (quiet periods) that are longer than a specified threshold.

Figure 6:
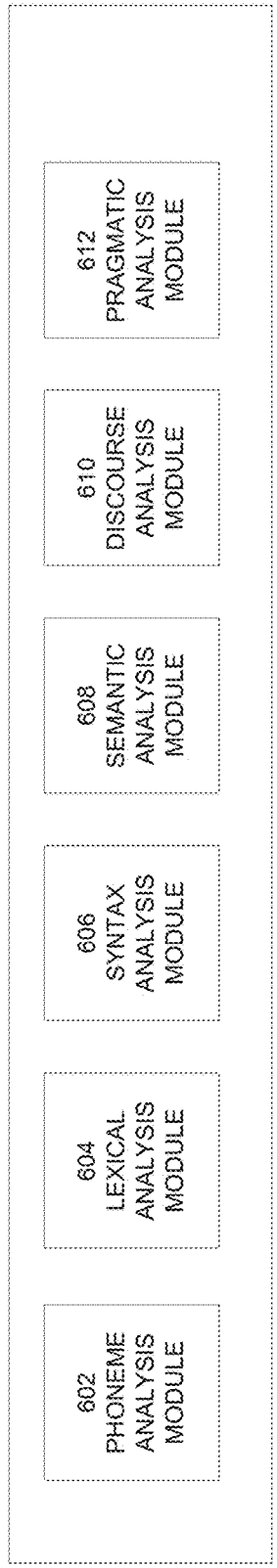
FIG. 6 illustrates an example natural language processing engine.

FIG. 6 illustrates an example implementation of the natural language processing engine 406. A phoneme analysis module 602 parses the incoming speech into phonemes. Optionally, a finite state transducer is used to perform such parsing. Optionally, the phoneme analysis module 602 may identify a phoneme boundary based, at least in part, on a detection of a rapid change in amplitude. Optionally, a statistical structure that encodes the probability of a sequence of events (e.g., one or more hidden Markov models) may be utilized to perform such parsing. For example, the hidden Markov model may be utilized to determine the probability of occurrence of different possible sequences of phonemes (e.g., using a triplet of phonemes). By way of illustration, optionally the phoneme analysis module 602 may analyze a speech segment, an immediately preceding speech segment, and an immediately following speech segment as a triplet. Triplets may be staggered. The phoneme analysis module 602 may compare a given triplet again stored reference phoneme data accessed from memory to identify potential matches. A match probability may be generated based on the comparison. The phoneme analysis module 602 may generate a temporal sequence of identified phonemes that correspond to the original speech signal. The phonemes may then be mapped to words (where a word may include one or more phonemes).

A lexical analysis module 604 divides the text into paragraphs, sentences, and words. A syntax analysis module 606 analyzes the validity of a sentence according to grammar rules. Optionally, context free grammar is used. By way of example, if a potential interpretation of an element of speech (e.g., a phrase or sentence) violates a grammar rule, the interpretation may be rejected and/or the interpretation may be marked as a potential health status indicator. By way of illustration, if a potential interpretation provides the following phrase "The door went out of I", because the interpretation violates grammatical rules, the interpretation may be rejected and/or the interpretation may be marked as a potential health status indicator (e.g., indicating that the speaker is under the influence of mind altering drug or is suffering from a stroke).

A semantic analysis module 608 analyzes the real meaning from the text. For example, the semantic analysis module 608 may assign text elements respective logical and grammatical roles. The semantic analysis module 608 may analyze context in the surrounding text and the text structure to disambiguate the proper meaning of words that have more than one definition. The semantic analysis module 608 may analyze the logical structure of a given phrase, clause, sentence, or paragraph to identify the most relevant elements in the text and identify the topic discussed. The semantic analysis module 608 may also understand the relationships between different concepts in the text and use such understanding to understand the subject of the text.

For example, the semantic analysis module 608 may determine that a unit of speech is about "technology" even if the unit of speech does not include the word "technology" but does include words or phrases that are related to the concept of "technology", such as "bandwidth", "streaming", "display resolution," etc. By way of further example, if a potential meaning of an element of speech (e.g., a phrase or sentence) does not make logical sense (e.g., "the giant tiny dog"), the potential meaning may be rejected and/or the potential meaning may be marked as a potential health status indicator (e.g., indicating that the speaker is under the influence of mind altering drug or is suffering from a stroke).

By way of yet further example, if the identified topic of sequential units of text (e.g., clauses within a sentence or from one sentence to another sentence) or nearby text (within a threshold number of sentences or clauses) indicate that the speaker is rapidly switching topics more than a threshold number of times, the potential meaning of a given unit of speech may be rejected and/or the rapid changes in subject may be marked as a potential health status indicator (e.g., indicating that the speaker is under the influence of mind altering drug or is suffering from a stroke). For example, if the identified topic of a first sentence is "cars" and the identified topic of a next sentence is "aliens", and the identified topic of a still next sentence is "headache", such rapid changes in subject may indicate that the speaker is having mental processing issues.

A discourse analysis module 610 analyzes the text and may identify the discourse relationships between clauses, sentences, and/or paragraphs (e.g., where the meaning of a sentence may depend upon the meaning of the immediately preceding sentence). For example, a given sentence may provide elaboration or a contrast with a preceding sentience. The discourse analysis module 610 may also analyze text to identify a text act, such as a question, assertion, etc. The discourse analysis module 610 may identify discourse that indicates a possible health status of the speaker.

A pragmatic analysis module 612 analyzes the text and may reinterpret what was said to determine what was actually meant. For example, the pragmatic analysis module 610 may know how units of speech (e.g., sentences) are used in different situations and how use affects the interpretation of the sentence. Thus, the pragmatic analysis module 612 may determine the likely intention of the speaker and the conversation to aid in the interpretation of the unit of speech.

Figure 7:
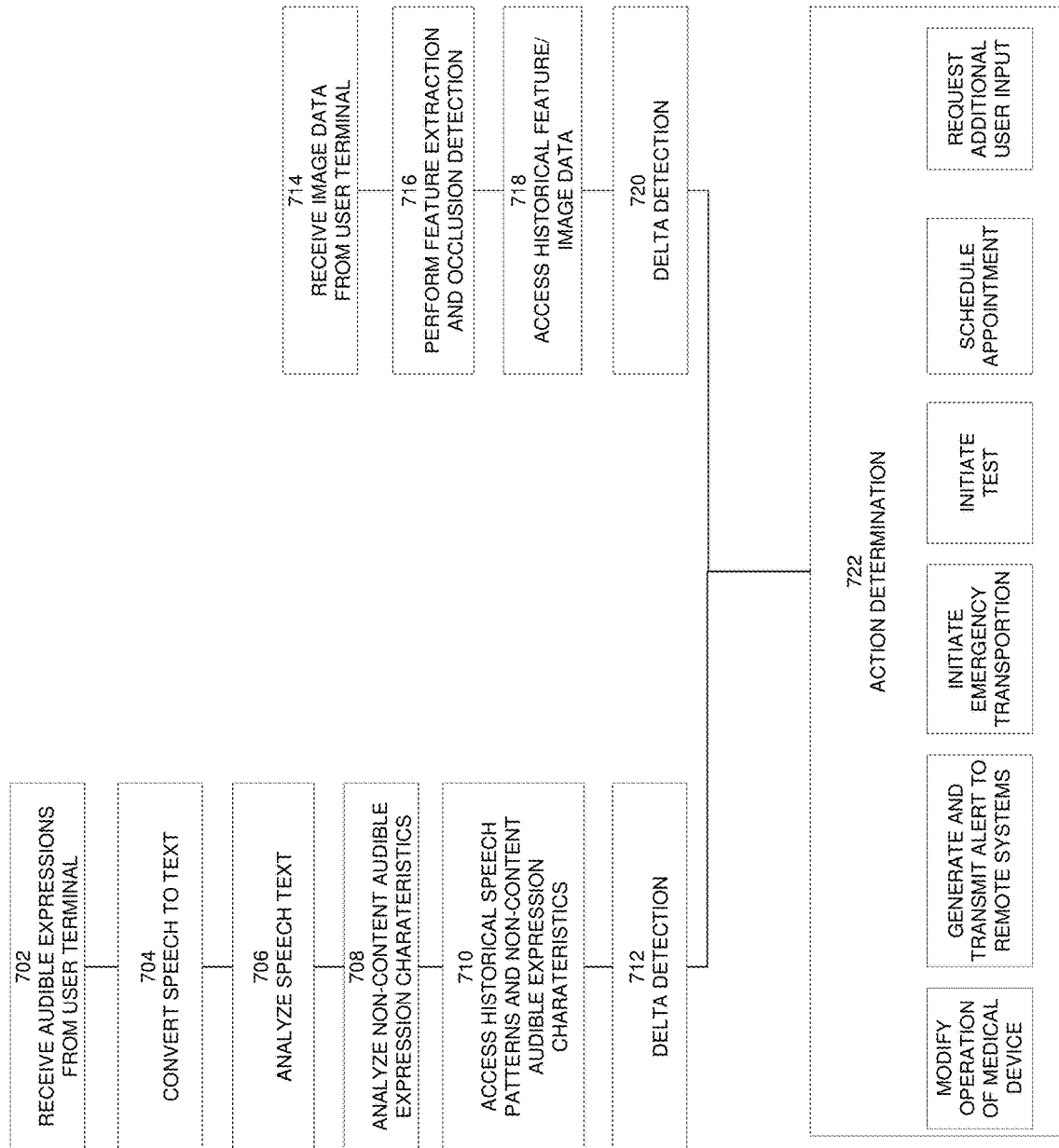
FIG. 7 illustrates an example process.

FIG. 7 illustrates a process that may be implemented using the example speech processing system and image processing system described herein. As will be described, the process may perform an analysis of both speech content and acoustic-phonetic properties of a user's to determine if a user has an elevated or immediate need for attention. The process may also optionally analyze images of the user to determine if the user has an elevated or immediate need for attention. The process may optionally be utilized in conjunction with an electronic notebook application, described elsewhere herein.

At block 702, audible expressions from the user is received (e.g., over a network) from a user terminal microphone. At block 714, images (e.g., still and/or video images that are optionally streamed from the user terminal) are received from a user terminal camera. The audible expressions and images may be recorded at different times or at the same time (e.g., while the user is recording a self-portrait ("selfie")) and included in the same video file. For example, the audible expressions and images may be received during a check-in process initiated by the notebook application, where the notebook application prompts the user to provide certain information (e.g., how the user is feeling, is the user taking prescribed medication, is the user following a treatment plan, etc.). Optionally, the user may initiate the recording.

At block 704, the audible expressions are converted to speech using a natural language processing engine (e.g., natural language processing engine 406) in a speech-to-text operation. Optionally, non-decipherable speech is identified as such and a corresponding tag is assigned. Optionally, where a word is slurred or broken, the correct textual spelling of the word and the phonetic "as pronounced" spelling of the word is generated. For example, if the user spoke the word "pleash", the natural language processing engine may convert the word to the text "please" and may also provide the text "pleash", with an indication as to which is the correct spelling and which is the spelling corresponding to how the word was actually pronounced.

At block 706, the content of the text is analyzed as similarly discussed elsewhere herein. For example, syntax, semantics, discourse, and/or pragmatic analysis may be applied to the text. Keywords may be identified that indicate the user's health status (e.g., physical and/or mental health status). Disjointed speech, illogical speech, repetitive speech, rapid changes in subject, word interjections, phrase interjections, word omissions, word revisions, broken suffixes, and/or other potential health status indicators may be identified based on the text.

At block 708, audible characteristics of speech may be analyzed (e.g., that are content independent). For example, as similarly discuss elsewhere herein, some or all of the following may be monitored and identified: incomplete closure of the vocal tract, improper onsets and offsets of stop and affricate closures, vocal tract constriction within a vowel segment, levels and increases in jitter and/or shimmer, variations in pitch period when speaking vowels, pitch and variations in pitch, volume levels, intakes of air, and/or other indications of vocal tract formation and muscle control, which may indicate health issues.

At block 710, historical speech and non-content audible expression characteristics data for the user is accessed from a data store. Optionally, the request for historical speech and non-content audible expression characteristics data is filtered so that only historical data that is relevant to the current speech and content-independent audible expression characteristics is accessed.

At block 712, changes in speech and non-content audible expression characteristics are determined by comparing the current and historical speech and non-content audible expression characteristics data. A change may be identified based on thresholds. By way example, if a speech rapidity delta threshold is set to 20%, than if the rapidity of the current speech is within 20% of the historical speech, the change in speech rapidity may be characterized as within normal variations (effectively no change). If, on the other hand, the rapidity of the current speech is more than 20% faster than that of the historical speech, the change in speech rapidity may be characterized as indicating a potential change in health status. By way of further example, the current pitch period when speaking vowels is within 11% of the historical speech, the change in pitch period may be characterized as within normal variations (effectively no change). If, on the other hand, the pitch period is more than 11% slower than that of the historical speech, the change in speech pitch period may be characterized as indicating a potential change in health status.

At block 716, feature extraction and occlusion detection may be performed. The process may detect and identify the user's face in an image. For example, the process may generate a facial model based on the features and compare it with a library of facial models associated with user identifiers, and determine if the facial model based on the image match a historical facial model of the user. The generated facial model may also be used to detect the user's health status. For example, the facial model may be analyzed to detect if any part of the user's face (e.g., cheek, lips, forehead, etc.) is drooping or twitching, which may indicate an adverse health status (e.g., stroke, seizure, etc.). In addition, the facial model may be analyzed to determine the degree to which user's eyelids are covering the user's eyes (e.g., and in particular, the pupils), which may indicate the user's current health status. It is understood, that the functions performed at block 716 may optionally be in parallel with the speech/audible expression functions.

At block 716, historical image data (e.g., facial feature data, eye occlusion data, facial models, etc.) for the user is accessed from a data store.

At block 718, changes in features and eye occlusion are determined by comparing the current and historical features and eye occlusion data. A change may be identified based on thresholds. By way example, if the detected lip droop is within 5% of the historical lip droop, the change in lip droop period may be characterized as within normal variations (effectively no change). If, on the other hand, the current lip droop is more than 5% than that of the historical lip droop, the change in lip droop period may be characterized as indicating a potential change in health status.

At block 722, an action determination and initiation may be performed based on the data identified or generated at other stages of the process (e.g., based on the outputs of block 704, 706, 708, 712, 716, and/or 720) and on one or more accessed rules. As part of the action determination process, one or more potential diagnosis may be generated (e.g., based on the outputs of block 704, 706, 708, 712, 716, and/or 720) and/or previously generated diagnosis may be utilized.

For example, as similarly discussed above, the actions may include modification of the operation a medical device. By way of illustration, if a determination is made that the user may be undergoing a hypoglycemia episode (based on a detection that the user has trouble speaking, appears confused, is undergoing a seizure, has poor motor control, etc.), the process may cause an insulin pump to inject the user with insulin by wirelessly transmitting an instruction to the pump, or by transmitting a corresponding recommendation to a remote system (which may then transmit the instruction to the pump).

By way of further example, the actions may include initiating emergency transportation to take the user to a medical facility (e.g., an emergency room). For example, the process may transmit an address corresponding to the user's location and the address of the medical facility to an autonomous or non-autonomous vehicle. The vehicle may utilize the address information to navigate to the user and then to navigate (with the user in the vehicle) to the medical facility.

By way of yet further example, the actions may include initiating a medical test on the user. The test may be conducted using sensors local to the user (e.g., a blood pressure sensor, an eye pressure sensor, a temperature sensor, a blood sensor, etc.) and the results may be transmitted to designated destinations (e.g., one or more of the user's medical support team). Optionally, a test may be scheduled at a medical testing facility and the date and location of the test may be added to the user's calendar. Optionally, other appointments with service providers may be scheduled and added to the user's calendar.

Figure 8:
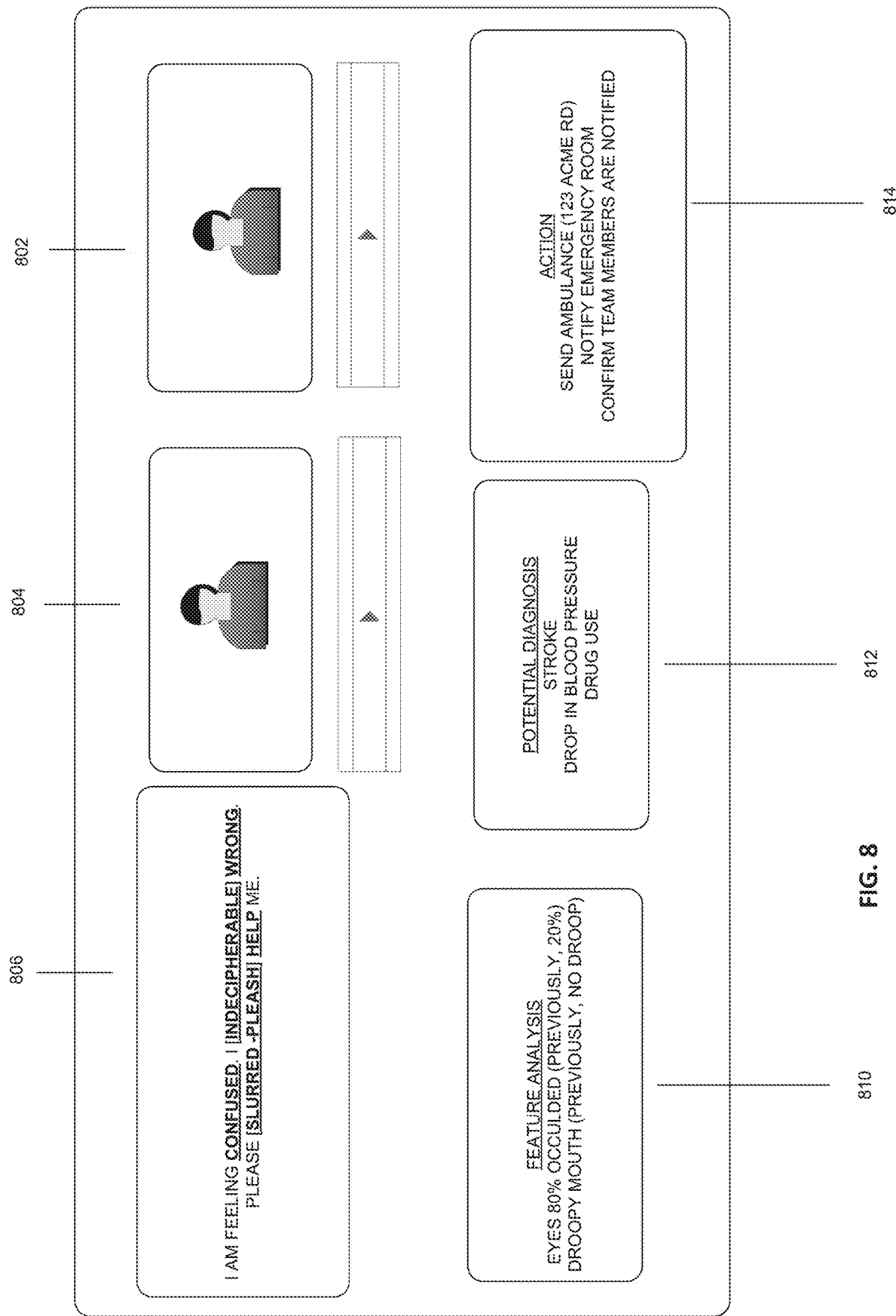
FIG. 8 illustrates an example user interface.

By way of further example, the actions may include the generation and transmission of a notification/alert to one or more destinations, such as the example notification illustrated in FIG. 8. The notification may include (e.g., via a file or a link to a file) a video 802 (including an audio tract) of the user that triggered the notification. The video 802 may be the complete video received from the user terminal, or the video may be trimmed to only include the video/audio that caused the trigger (optionally include a set number of pre and/or post video/audio content). The video 802 may be displayed by a content player with associated controls (e.g., play, pause, rewind, fast forward, scrubber controls). Optionally, the notification may include (e.g., via a file or a link to a file) the historical video 804 (including an audio tract) used in the comparison with the current video. The video 804 may be displayed by a content player with associated controls (e.g., play, pause, rewind, fast forward, scrubber controls).

Optionally, the notification may include a text area 806 that provides some or all of the text obtained via the speech to text operation. Optionally, unintelligible speech is identified (e.g., with a text and/or graphic tag). Optionally, where a word is slurred or otherwise malformed, the correct spelling for the word and the phonetic spelling for the word corresponding to the user's actual pronunciation are provided. Optionally, the results of the facial feature analysis 810 that indicate a potential health issue are provided. Optionally, a listing of potential diagnosis 812 is provided (e.g., stroke, high blood pressure, load blood pressure, drug use, seizure, etc.). Optionally, a listing of taken actions and/or recommended actions 814 is provided (e.g., ambulance dispatched to user location, notification of emergency room to expect user/patient, confirm that user team members have been notified (e.g., request that team members send a confirmation response and determine if the confirmation response has been received), etc.).

Optionally, the speech and/or facial analysis described above may be used to detect medical states of users prior to or while operating dangerous machinery (e.g., cranes, lathes, drills, saws, power plants, mining equipment, etc.) or vehicles (e.g., planes, ships, trains, buses, automobiles, motorcycles, and/or the like), where certain medical states may indicate user impairment with respect to operating such vehicles or equipment. For example, a device may be used to capture user speech and/or user images at a check-in terminal for pilots, train engineers, bus drivers, equipment operators, or the like, where the check-in terminal is equipped with a microphone and/or camera (e.g., as part of a mental status examination). By way of further example, the machinery or vehicle may be equipped with a device to capture user speech and/or user images prior to or while the user is operating the machinery or vehicle. The user's speech and/or facial images may also be captured via a user device (e.g., a user phone, laptop, wearable, or other such device). The speech and/or images may be analyzed to determine if the user is under the influence of drugs or alcohol, or has a medical status that may impair the user's ability to safely operate the machinery or vehicle. If a determination is made that the user may be unable to safely operate the machinery or vehicle, the machinery or vehicle may be automatically disabled (e.g., so that the machine may not be operated or so the vehicle is not drivable or flyable) or switched to autopilot (where appropriate). In addition or instead, one or more notifications may be transmitted to one or more destinations (e.g., an employer, a government regulatory agency, security personnel, etc.), and a notification may be transmitted to and/or presented to the user regarding such determined impairment.

A user's impairment may be scored based on detected speech and/or facial characteristics, such as those described above (e.g., slurring of speech, drooping eyelids, etc.). Certain characteristics, such as changes in formation of phonemes (e.g., that indicate slurring of speech) may be weighted more heavily than changes in rapidity of speech. Different thresholds for detected or inferred user impairment (e.g., caused by alcohol or drug use) may be set for different vehicle types, wherein once a certain threshold is reached certain actions are performed (e.g., disabling of vehicle, transmission of notifications, etc.). For example, a lower threshold of detected impairment may be set for a pilot of a passenger jet than for an operator of a forklift.

Thus, processes and techniques are described that may be used to receive, manage and process the recording, arrangement, text processing, word recognition, and/or review of information for or in an electronic notebook.

The methods and processes described herein may have fewer or additional steps or states and the steps or states may be performed in a different order. Not all steps or states need to be reached. The methods and processes described herein may be embodied in, and fully or partially automated via, software code modules executed by one or more general purpose computers. The code modules may be stored in any type of computer-readable medium or other computer storage device. Some or all of the methods may alternatively be embodied in whole or in part in specialized computer hardware. The systems described herein may optionally include displays, user input devices (e.g., touchscreen, keyboard, mouse, voice recognition, etc.), network interfaces, etc.

The results of the disclosed methods may be stored in any type of computer data repository, such as relational databases and flat file systems that use volatile and/or non-volatile memory (e.g., magnetic disk storage, optical storage, EEPROM and/or solid state RAM).

The various illustrative logical blocks, modules, routines, and algorithm steps described in connection with the embodiments disclosed herein can be implemented as electronic hardware, computer software, or combinations of both. To clearly illustrate this interchangeability of hardware and software, various illustrative components, blocks, modules, and steps have been described above generally in terms of their functionality. Whether such functionality is implemented as hardware or software depends upon the particular application and design constraints imposed on the overall system. The described functionality can be implemented in varying ways for each particular application, but such implementation decisions should not be interpreted as causing a departure from the scope of the disclosure.

Moreover, the various illustrative logical blocks and modules described in connection with the embodiments disclosed herein can be implemented or performed by a machine, such as a general purpose processor device, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor device can be a microprocessor, but in the alternative, the processor device can be a controller, microcontroller, or state machine, combinations of the same, or the like. A processor device can include electrical circuitry configured to process computer-executable instructions. In another embodiment, a processor device includes an FPGA or other programmable device that performs logic operations without processing computer-executable instructions. A processor device can also be implemented as a combination of computing devices, e.g., a combination of a DSP and a microprocessor, a plurality of microprocessors, one or more microprocessors in conjunction with a DSP core, or any other such configuration. Although described herein primarily with respect to digital technology, a processor device may also include primarily analog components. A computing environment can include any type of computer system, including, but not limited to, a computer system based on a microprocessor, a mainframe computer, a digital signal processor, a portable computing device, a device controller, or a computational engine within an appliance, to name a few.

The elements of a method, process, routine, or algorithm described in connection with the embodiments disclosed herein can be embodied directly in hardware, in a software module executed by a processor device, or in a combination of the two. A software module can reside in RAM memory, flash memory, ROM memory, EPROM memory, EEPROM memory, registers, hard disk, a removable disk, a CD-ROM, or any other form of a non-transitory computer-readable storage medium. An exemplary storage medium can be coupled to the processor device such that the processor device can read information from, and write information to, the storage medium. In the alternative, the storage medium can be integral to the processor device. The processor device and the storage medium can reside in an ASIC. The ASIC can reside in a user terminal. In the alternative, the processor device and the storage medium can reside as discrete components in a user terminal.

Conditional language used herein, such as, among others, "can," "may," "might," "may," "e.g.," and the like, unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without other input or prompting, whether these features, elements and/or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

Disjunctive language such as the phrase "at least one of X, Y, Z," unless specifically stated otherwise, is otherwise understood with the context as used in general to present that an item, term, etc., may be either X, Y, or Z, or any combination thereof (e.g., X, Y, and/or Z). Thus, such disjunctive language is not generally intended to, and should not, imply that certain embodiments require at least one of X, at least one of Y, or at least one of Z to each be present.

While the phrase "click" may be used with respect to a user selecting a control, menu selection, or the like, other user inputs may be used, such as voice commands, text entry, gestures, etc. User inputs may, by way of example, be provided via an interface, such as via text fields, wherein a user enters text, and/or via a menu selection (e.g., a drop down menu, a list or other arrangement via which the user can check via a check box or otherwise make a selection or selections, a group of individually selectable icons, etc.). When the user provides an input or activates a control, a corresponding computing system may perform the corresponding operation. Some or all of the data, inputs and instructions provided by a user may optionally be stored in a system data store (e.g., a database), from which the system may access and retrieve such data, inputs, and instructions. The notifications/alerts and user interfaces described herein may be provided via a Web page, a dedicated or non-dedicated phone application, computer application, a short messaging service message (e.g., SMS, MMS, etc.), instant messaging, email, push notification, audibly, a pop-up interface, and/or otherwise.

The user terminals described herein may be in the form of a mobile communication device (e.g., a cell phone), laptop, tablet computer, interactive television, game console, media streaming device, head-wearable display, networked watch, etc. The user terminals may optionally include displays, user input devices (e.g., touchscreen, keyboard, mouse, voice recognition, etc.), network interfaces, etc.

While the above detailed description has shown, described, and pointed out novel features as applied to various embodiments, it can be understood that various omissions, substitutions, and changes in the form and details of the devices or algorithms illustrated can be made without departing from the spirit of the disclosure. As can be recognized, certain embodiments described herein can be embodied within a form that does not provide all of the features and benefits set forth herein, as some features can be used or practiced separately from others. The scope of certain embodiments disclosed herein is indicated by the appended claims rather than by the foregoing description. All changes which come within the meaning and range of equivalency of the claims are to be embraced within their scope.

What is claimed is:

1. An electronic device configured to process audible expressions from users, comprising:
    a network interface;
    at least one computing device; and
    computer readable memory including instructions operable to be executed by the at least one computing device to perform a set of actions, configuring the at least one computing device to:
    receive in real time, over a network via the network interface, a digitized human vocal expression of a first user from a first source;
    process the received digitized human vocal expression, received in real time, using digital signal processing to convert the digitized audible expression from a time domain to a frequency domain;
    use the processed digitized human vocal expression to determine characteristics of the human vocal expression by at least:
        determining a power spectrum of the human vocal expression; and
        detecting quiet time between words using the power spectrum of the human vocal expression to determine pauses and length of pauses in speech in the human vocal expression and to determine how rapidly the first user is speaking in the human vocal expression;
    use a natural language module to:
        convert at least portion of the digitized human vocal expression to text; and
        detect violations of grammar rules in the text obtained from the human vocal expression to obtain detected grammar violations;
    compare the determined characteristics of the human vocal expression with baseline, historical characteristics of human vocal expressions associated with the first user to identify changes in human vocal expression characteristics of the first user as identified vocal changes, including changes in how rapidly the first user is speaking;
    weight, using a first weight, a first identified change, of the identified vocal changes, with respect to a first vocal expression characteristic of the first user, the first vocal characteristic comprising changes in how rapidly the first user is speaking;
    weight, using a second weight, a second identified change, of the identified vocal changes, with respect to a second vocal expression characteristic of the first user;
    weight, using a third weight, the detected grammar violations;
    infer a change in health status of the first user, the inferred change in health status comprising a post-traumatic stress disorder (PTSD) episode, based at least in part on:
        the weighted first identified change with respect to the first vocal expression characteristic of the first user, the first vocal characteristic comprising changes in how rapidly the first user is speaking,
        the weighted second identified change with respect to the second vocal expression characteristic of the first user, and the weighted third identified change with respect to the detected grammar violations, and based at least in part on the inferred change in health status, comprising the post-traumatic stress disorder (PTSD) episode, of the first user, cause a first action is to be taken, the first action comprising causing a vehicle to be prevented from being drivable or flyable.

2. The electronic device as defined in claim 1, wherein the electronic device is configured to estimate a quasiperiodic signal period of the human vocal expression and determine a pitch using the estimated quasiperiodic signal period and use the determined pitch in inferring the change in health status of the first user.

3. The electronic device as defined in claim 1, wherein the electronic device is configured to determine a cepstrum pitch using an inverse Fourier transform (IFT) of a logarithm of an estimated spectrum of a human vocal expression signal and use the determined pitch in inferring the change in health status of the first user.

4. The electronic device as defined in claim 1, wherein the electronic device is configured to determine a volume of the human vocal expression based at least in part on peak heights in the power spectrum of the human vocal expression and use the determined volume in inferring the change in health status of the first user.

5. The electronic device as defined in claim 1, wherein the electronic device is configured to determine as to how rapidly the first user is speaking based at least in part on a determination of how many words are spoken by the first user over a first period of time.

6. The electronic device as defined in claim 1, wherein detecting quiet time between words using the power spectrum of the human vocal expression to determine pauses and length of pauses in speech in the human vocal expression, further comprises identifying pauses in speech in the human vocal expression using both the power spectrum and a magnitude spectrum of the human vocal expression.

7. The electronic device as defined in claim 1, wherein the electronic device is configured to determine if an occlusion of eyes of the first user by eyelids of the first user indicates an adverse health state.

8. An electronic device, comprising:
a network interface;
at least one computing device; and
computer readable memory including instructions operable to be executed by the at least one computing device to perform a set of actions, configuring the at least one computing device to:
access a digitized human vocal expression of a first user received in real time from a first source converted from a time domain to a frequency domain;
use the converted digitized human vocal expression to determine characteristics of the human vocal expression, by at least:
detecting quiet time using identified pauses and length of pauses between words in speech in the human vocal expression, and
determining how rapidly the first user is speaking in the human vocal expression using the detected quiet time;
use natural language processing to:
convert at least a portion of the digitized human vocal expression to text; and
detect violations of grammar rules in the text obtained from the human vocal expression to obtain detected grammar violations;

compare the determined characteristics of the human vocal expression with baseline, historical characteristics of human vocal expressions associated with the first user to identify changes in human vocal expression characteristics of the first user as identified vocal changes, including changes in how rapidly the first user is speaking;

weight, using a first weight, a first identified change, of the identified vocal changes, with respect to a first vocal expression characteristic of the first user, the first vocal characteristic comprising changes in how rapidly the first user is speaking;

weight, using a second weight, a second identified change, of the identified vocal changes, with respect to a second vocal expression characteristic of the first user;

weight, using a third weight, the detected grammar violations; and infer a change in health status, the inferred change in health status comprising a post-traumatic stress disorder (PTSD) episode, of the first user based at least in part on:

the weighted first identified change with respect to the first vocal expression characteristics of the first user, the first vocal characteristic comprising changes in how rapidly the first user is speaking, the weighted second identified change with respect to the second vocal expression characteristic of the first user, the weighted detected grammar violations; and based at least in part on the inferred change in health status, comprising the post-traumatic stress disorder (PTSD) episode, of the first user, cause a first action is to be taken, the first action pertaining to operation of machinery.

9. The electronic device as defined in claim 8, wherein the electronic device comprises a vehicle, and the first action comprises inhibiting the vehicle from being drivable or flyable.

10. The electronic device as defined in claim 8, wherein the determined characteristics of the human vocal expression comprise pitch, and the electronic device is configured to estimate a quasiperiodic signal period of the human vocal expression and determine the pitch using the estimated quasiperiodic signal period and use the determined pitch in inferring the change in health status of the first user.

11. The electronic device as defined in claim 8, wherein the determined characteristics of the human vocal expression comprise pitch, and the electronic device is configured to determine a cepstrum pitch using an inverse Fourier transform (IFT) of a logarithm of an estimated spectrum of a human vocal expression signal and use the determined pitch in inferring the change in health status of the first user.

12. The electronic device as defined in claim 8, wherein the electronic device is configured to determine a volume of the human vocal expression based at least in part on peak heights in a power spectrum of the human vocal expression and use the determined volume in inferring the change in health status of the first user.

13. The electronic device as defined in claim 8, wherein the electronic device is configured to determine how rapidly the first user is speaking based at least in part on a determination of how many words are spoken over a first period of time.

14. The electronic device as defined in claim 8, wherein detecting quiet time using identified pauses and length of pauses in speech in the human vocal expression further comprises identifying pauses in speech in the human vocal expression using both a power and a magnitude spectrum of the human vocal expression.

15. The electronic device as defined in claim 8, wherein the electronic device is configured to determine if an occlusion of eyes of the first user by eyelids of the first user indicates an adverse health state.

16. The electronic device as defined in claim 8, wherein the first action comprises generation of a notification and provision of the notification to one or more destinations, wherein the notification comprises:
   at least a portion of the received digitized human vocal expression,
   text corresponding to at least a portion of the received digitized human vocal expression, and
   at least one received image of the first user.

17. A computer implemented method, comprising:
   accessing at a computer system comprising one or more computing devices, a digitized human vocal expression of a first user received in real time from a first source converted from a time domain to a frequency domain;
   using the converted digitized human vocal expression to determine characteristics of the human vocal expression, by at least:
   detecting quiet time using identified pauses and length of pauses in speech in the human vocal expression, and
   determining how rapidly the first user is speaking in the human vocal expression using the detected quiet time;
   using natural language processing to:
      convert at least a portion of the digitized human vocal expression to text;
      detect violations of grammar rules in the text obtained from the human vocal expression to obtain detected grammar violations;
   comparing the determined characteristics of the human vocal expression with baseline, historical characteristics of human vocal expressions associated with the first user to identify changes in human vocal expression characteristics of the first user as identified vocal changes, including changes in how rapidly the first user is speaking;
   weighting, using a first weight, a first identified change, of the identified vocal changes, with respect to a first vocal expression characteristic of the first user, the first vocal characteristic comprising changes in how rapidly the first user is speaking,
   weighting, using a second weight, a second identified change, of the identified vocal changes, with respect to a second vocal expression characteristic of the first user;
   weighting, using a third weight, the detected grammar violations; and
   inferring a change in health status, comprising a post-traumatic stress disorder (PTSD) episode, of the first user based at least in part on:
   the weighted first identified change with respect to the first vocal expression characteristic of the first user, the first vocal characteristic comprising changes in how rapidly the first user is speaking,
   the weighted second identified change with respect to the second vocal expression characteristic of the first user;
   the weighted detected grammar violations; and
      based at least in part on the inferred change in health status, comprising the post-traumatic stress disorder (PTSD) episode, of the first user, causing a first action is to be taken, the first action pertaining to operations of machinery.

18. The computer implemented method as defined in claim 17, wherein the first device comprises a vehicle, and the first action comprises causing the vehicle to be prevented from being drivable or flyable.

19. The computer implemented method as defined in claim 17, the method further comprising determining a volume of the human vocal expression based at least in part on peak heights in a power spectrum of the human vocal expression and using the determined volume in inferring the change in health status of the first user.

20. The computer implemented method as defined in claim 17, the method further comprising:
   processing one or more images of the first user to detect occlusion of eyes of the first user by eyelids of the first user; and
   determining whether an occlusion of eyes of the first user by eyelids of the first user indicates an adverse health state,
   wherein the first action is caused to be taken based in part on the determination of whether an occlusion of eyes of the first user by eyelids of the first user indicates an adverse health state.

21. The computer implemented method as defined in claim 17, the method further comprising:
   wherein the first action comprises generating a notification and providing the notification to one or more destinations, wherein the notification comprises:
   at least a portion of the received digitized human vocal expression,
   text corresponding to at least a portion of the received digitized human vocal expression, and
   at least one received image.

* * * * *